United States Patent [19]

Baker et al.

[11] Patent Number: 4,952,587

[45] Date of Patent: Aug. 28, 1990

[54] PHYSIOLOGICALLY ACTIVE 1,2,4,-OXA- AND THIADIAZOLES

[75] Inventors: Raymond Baker, Much Hadham; John Saunders, Bishops Stortford; Christopher Swain, Duxford, all of England

[73] Assignee: Merck Sharp & Dohme Ltd., Hertfordshire, England

[21] Appl. No.: 306,007

[22] Filed: Feb. 3, 1989

[30] Foreign Application Priority Data

Feb. 12, 1988 [GB] United Kingdom ............... 8803317
May 6, 1988 [GB] United Kingdom ............... 8810789

[51] Int. Cl.⁵ ............... C07D 413/14; C07D 453/02; A61K 31/44; A61K 31/42
[52] U.S. Cl. ............... 514/305; 514/210; 514/212; 514/214; 514/299; 514/304; 514/323; 514/339; 514/361; 540/586; 540/603; 546/112; 546/126; 546/133; 546/137; 546/183; 546/201; 546/273; 548/128; 548/131
[58] Field of Search ............... 546/112, 126, 133, 137, 546/183, 196, 201, 202, 269, 273, 274; 548/128, 131; 540/582, 603; 514/210, 214, 212, 299, 304, 305, 323, 324, 320, 337, 339, 361, 364

[56] References Cited

U.S. PATENT DOCUMENTS 3,646,053 2/1972 Poletto et al. ............... 260/306.8
4,203,990 5/1980 Yen ............... 424/267
4,342,769 8/1982 Steinman et al. ............... 424/251

FOREIGN PATENT DOCUMENTS 0083566 7/1983 European Pat. Off.
0239309 9/1987 European Pat. Off.
0261763 3/1988 European Pat. Off.
2193633 2/1988 United Kingdom.

*Primary Examiner*—Mary C. Lee
*Assistant Examiner*—Bernard L. Dentz
*Attorney, Agent, or Firm*—Joseph F. DiPrima; Manfred Polk

[57] ABSTRACT

The present invention provides a compound of formula I or a salt or prodrug thereof:

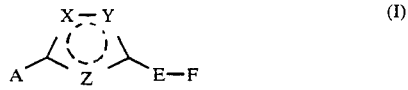

wherein the dotted circle represents one or two double bonds in any position in the 5-membered ring;
X, Y and Z independently represent oxygen, sulphur, nitrogen or carbon, provided that at least one of X, Y and Z represents oxygen, sulphur or nitrogen;
A represents a group of formula II:

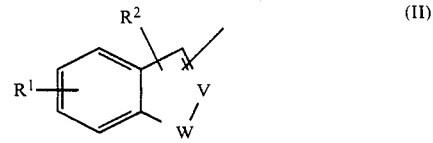

in which
$R^1$ represents hydrogen, hydroxy, $C_{1-6}$ alkyl, $C_{2-6}$ alkenyl, $C_{2-6}$ alkynyl, $C_{1-6}$ alkoxy, hydroxy($C_{1-6}$)alkyl, halogen, amino, cyano, $-CONR^6R^7$ or $-SO_2NR^6R^7$, in which $R^6$ and $R^7$ independently represent hydrogen, $C_{1-6}$ alkyl, $C_{2-6}$ alkenyl or $C_{2-6}$ alkynyl;
$R^2$ represents hydrogen, halogen, $C_{1-6}$ alkyl, $C_{1-6}$ alkoxy or $C_{1-6}$ alkylcarbonyl;
V represents nitrogen,

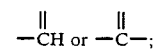

and
W represents oxygen, sulphur or

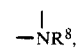

in which $R^8$ represents hydrogen, $C_{1-6}$ alkyl, $C_{2-6}$ alkenyl or $C_{2-6}$ alkynyl;
E represents a bond or a straight or branched alkylene chain containing from 1 to 5 carbon atoms, and optionally being substituted with hydroxy or phenyl; and
F represents:
  (a) a non-aromatic azacyclic or azabicyclic ring system; or
  (b) a group of formula $-NR^aR^b$, in which $R^a$ and $R^b$ independently represent hydrogen, $C_{1-6}$ alkyl, $C_{2-6}$ alkenyl, $C_{2-6}$ alkynyl or aryl($C_{1-6}$)alkyl; which compounds are useful in the treatment of psychotic disorders (e.g. schizophrenia and mania); anxiety; alcohol or drug withdrawal; pain; gastric stasis; gastric dysfunction (such as occurs with dyspepsia, peptic ulcer, reflux oesophagitis and flatulence); migraine, nausea and vomiting; and presenile and senile dementia.

5 Claims, No Drawings

PHYSIOLOGICALLY ACTIVE 1,2,4,-OXA- AND THIADIAZOLES

This invention relates to a class of 5-membered heterocyclic compounds having at least one heteroatom, which are useful in the treatment of psychotic disorders (e.g. schizophrenia and mania); anxiety; alcohol or drug withdrawal; pain; gastric stasis; gastric dysfunction (such as occurs with dyspepsia, peptic ulcer, reflux oesophagitis and flatulence); migraine, nausea and vomiting; and presenile and senile dementia (also known as Alzheimer's disease and senile dementia of the Alzheimer type respectively).

The present invention provides a compound of formula I or a salt or prodrug thereof:

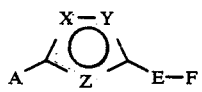
(I)

wherein the dotted circle represents one or two double bonds in any position in the 5-membered ring; X, Y and Z independently represent oxygen, sulphur, nitrogen or carbon, provided that at least one of X, Y and Z represents oxygen, sulphur or nitrogen;

A represents a group of formula II:

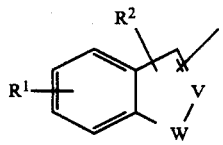
(II)

in which:

$R^1$ represents hydrogen, hydroxy, $C_{1-6}$ alkyl, $C_{2-6}$ alkenyl, $C_{2-6}$ alkynyl, $C_{1-6}$ alkoxy, hydroxy($C_{1-6}$)alkyl, halogen, amino, cyano, —$CONR^6R^7$ or —$SO_2NR^6R^7$, in which $R^6$ and $R^7$ independently represent hydrogen, $C_{1-6}$ alkyl, $C_{2-6}$ alkenyl or $C_{2-6}$ alkynyl;

$R^2$ represents hydrogen, halogen, $C_{1-6}$ alkyl, $C_{1-6}$ alkoxy or $C_{1-6}$ alkylcarbonyl;

V represents nitrogen,

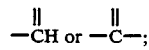

and

W represents oxygen, sulphur or

in which $R^8$ represents hydrogen, $C_{1-6}$ alkyl, $C_{2-6}$ alkenyl or $C_{2-6}$ alkynyl;

E represents a bond or a straight or branched alkylene chain containing from 1 to 5 carbon atoms, and optionally being substituted with hydroxy or phenyl; and F represents:

(a) a non-aromatic azacyclic or azabicyclic ring system; or (b) a group of formula —$NR^aR^b$, in which $R^a$ and $R^b$ independently represent hydrogen, $C_{1-6}$ alkyl, $C_{2-6}$ alkenyl, $C_{2-6}$ alkynyl or aryl ($C_{1-6}$)alkyl.

The ring shown as formula I may be, for example, a furan, thiophene, pyrrole, oxazole, thiazole, oxazoline, isoxazoline, thiazoline, oxadiazole, thiadiazole or imidazole ring, in particular a 1,2,4-oxadiazole, 1,3,4-oxadiazole, 1,2,4-thiadiazole or 1,3,4-thiadiazole ring. Preferably the ring is a 1,2,4-oxadiazole or 1,2,4-thiadiazole ring.

The group A is suitably an indole, benzofuran or benzthiophene, of formula IIA:

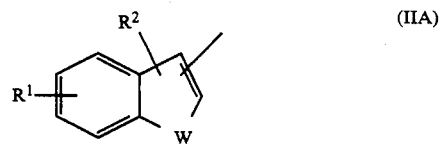
(IIA)

wherein $R^1$, $R^2$ and W are as defined above. Preferably, the group A represents an indole of structure IIB:

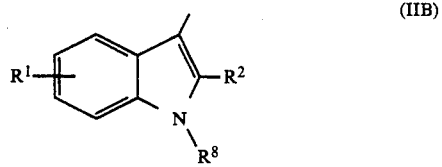
(IIB)

wherein $R^1$, $R^2$ and $R^8$ are as defined above. Preferably $R^1$ and $R^8$ independently represent hydrogen or methyl, and $R^2$ is hydrogen.

The alkylene chain E may be, for example, methylene, ethylene, 1-methylethylene, propylene, 2-methylpropylene, hydroxymethylene, 1-hydroxyethylene or phenylmethylene. Alternatively the group E may represent a single bond so that the group F is attached directly to the ring.

When the group F is an azacyclic or azabicyclic ring system, it is a non-aromatic ring system containing one nitrogen atom as the sole heteroatom. Suitably the ring system contains from 4 to 10 ring atoms, preferably from 5 to 9 ring atoms. The bicyclic systems may be fused, spiro or bridged. Examples of suitable ring systems include the following:

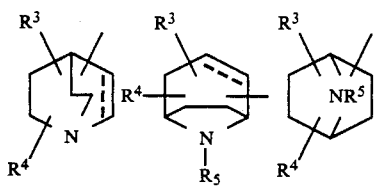

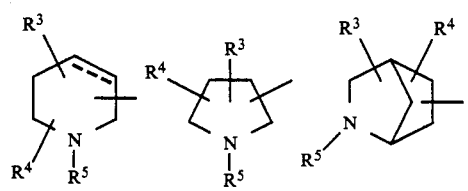

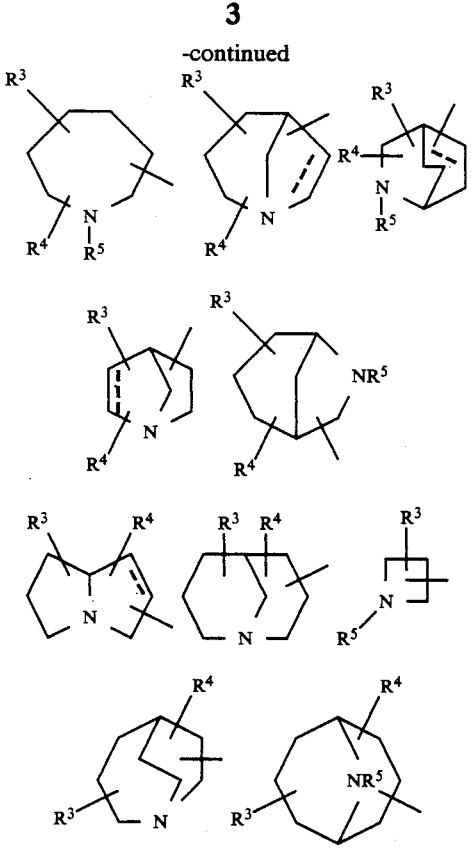

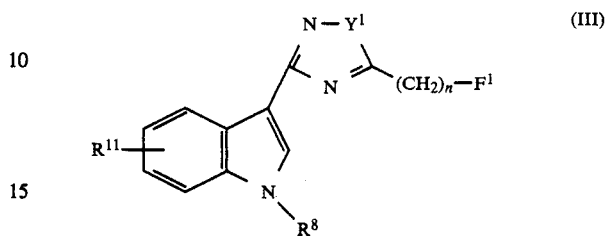

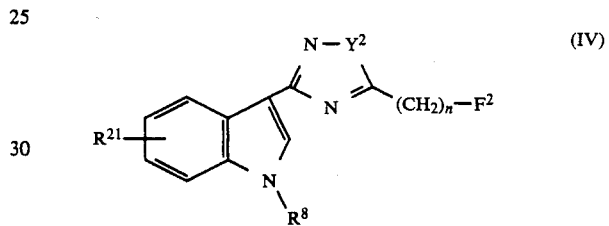

wherein the broken line represents an optional chemical bond;

$R^3$ and $R^4$ independently represent hydrogen, $C_{1-4}$ alkyl, $C_{2-4}$ alkenyl, $C_{2-4}$ alkynyl, halogen, $C_{1-4}$ alkoxy, hydroxy, carboxy or $C_{1-4}$ alkoxycarbonyl; or $R^3$ and $R^4$ together represent carbonyl; and $R^5$ represents hydrogen, $C_{1-4}$ alkyl, $C_{2-4}$ alkenyl or $C_{2-4}$ alkynyl.

It will be appreciated that the nitrogen atom in the azacyclic or azabicyclic ring will carry a lone pair of electrons.

It will equally be appreciated that the $R^3$ and $R^4$ substituents may be present at any position in the azacyclic or azabicyclic ring system, including the point of attachment to the group E. It will further be appreciated that the point of attachment of the azacyclic or azabicyclic ring system to the group E will be at any position of the ring system.

Suitably the group $R^3$ is hydrogen or methyl; and $R^4$ is hydrogen, $C_{1-4}$ alkoxy, $C_{1-4}$ alkyl or hydroxy, preferably methoxy, methyl or hydroxy. Preferably one or both of $R^3$ and $R^4$ is hydrogen.

Suitably the azacyclic or azabicyclic ring system is pyrrolidine, piperidine, tetrahydropyridine, azanorbornane, quinuclidine, isoquinuclidine, azabicyclo[3.2.1]octane or azabicyclo[3.3.1]nonane, any of which may be optionally substituted with methoxy, methyl or hydroxy.

When the group F represents $-NR^aR^b$, suitable examples of this group include amino; alkylamino such as methylamino; dialkylamino such as dimethylamino; and di(aralkyl)amino such as dibenzylamino.

The alkyl, alkenyl and alkynyl groups referred to with respect to any of the above formulae may represent straight, branched or cyclic groups. Thus, for example, suitable alkyl groups include methyl, ethyl, n- or iso-propyl, n-, sec-, iso- or tert-butyl, and cyclopropyl, cyclobutyl, cyclopentyl or cyclohexyl; suitable alkenyl groups include vinyl and allyl; and suitable alkynyl groups include propargyl.

One sub-class of compounds within the scope of the present invention is represented by formula III:

wherein $R^8$ is as defined above; $Y^1$ represents oxygen or sulphur; n is zero, 1 or 2; $R^{11}$ represents hydrogen, hydroxy or hydroxymethyl; and $F^1$ represents a group of formula $-NR^aR^b$ as defined above.

A further sub-class of compounds within the scope of the present invention is represented by formula IV:

wherein $R^8$ is as defined above; $Y^2$ represents oxygen or sulphur; n is zero, 1 or 2; $R^{21}$ represents hydrogen, halogen, cyano or $C_{1-6}$ alkyl; and $F^2$ represents a non-aromatic azacyclic or azabicyclic ring system; in particular wherein $F^2$ represents piperidine, tetrahydropyridine, azanorbornane, quinuclidine, isoquinuclidine, 8-azabicyclo[3.2.1]-octane or azabicyclononane.

Most of the compounds of this invention have at least one asymmetric centre and often more than one; and can therefore exist both as enantiomers and as diastereoisomers. In particular, those compounds possessing an unsymmetrical azabicyclic ring system may exist as exo and endo diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful for the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Salts of amine groups may also comprise the quaternary ammonium salts in which the amino nitrogen atom carries an alkyl, alkenyl, alkynyl or aralkyl group. Where the novel compound carries a carboxylic acid group the invention also contemplates salts thereof, preferably non-toxic pharmaceutically acceptable salts thereof, such as the sodium, potassium and calcium salts thereof.

Specific compounds of this invention include:
3-[3-(1-methylindol-3-yl)-1,2,4-oxadiazol-5-yl]-1-azabicyclo[2.2.2]octane;
2-[3-(1-methylindol-3-yl)-1,2,4-oxadiazol-5-yl]-1-azabicyclo[2.2.2]octane;
1-methyl-3-[5-dimethylaminomethyl-1,2,4-oxadiazol-3-yl]indole;
[3-(1-methylindol-3-yl)-1,2,4-oxadiazol-5-yl]methyl-trimethylammonium iodide;
1-methyl-4-[3-(1-methylindol-3-yl)-1,2,4-oxadiazol-5-yl]piperidine;
1,1-dimethyl-4-[3-(1-methylindol-3-yl)-1,2,4-oxadiazol-5-yl]piperidinium iodide;
1-methyl-3-[3-(1-methylindol-3-yl)-1,2,4-oxadiazol-5-yl]piperidine;
1,1-dimethyl-3-[3-(1-methylindol-3-yl)-1,2,4-oxadiazol-5-yl]piperidinium iodide;
1-methyl-3-[5-aminomethyl-1,2,4-oxadiazol-3-yl]indole;
1-methyl-3-[5-methylaminomethyl-1,2,4-oxadiazol-3-yl]-indole;
3-[3-(5-fluoro-1-methylindol-3-yl)-1,2,4-oxadiazol-5-yl]-1-azabicyclo[2.2.2]octane;
1-methyl-3-[5-dimethylaminoethyl-1,2,4-oxadiazol-3-yl]indole;
3-[3-(1-methylindol-3-yl)-1,2,4-oxadiazol-5-yl]-8-methyl-8-azabicyclo[3.2.1]octane;
3-[3-(1-methylindol-3-yl)-1,2,4-oxadiazol-5-yl]-1,2,5,6-tetrahydropyridine;
3-[3-(1-methylindol-3-yl)-1,2,4-oxadiazol-5-yl]-1-methyl-1,2,5,6-tetrahydropyridine;
3-[5-(1-methylindol-3-yl)-1,2,4-oxadiazol-3-yl]-1-azabicyclo[2.2.2]octane;
3-[4-(5-cyanoindol-3-yl)-1,3-thiazol-2-yl]-1-methyl-1,2,5,6-tetrahydropyridine;
3-[3-(1-methylindol-3-yl)-1,2,4-oxadiazol-5-yl]-1-aza-2-methoxybicyclo[2.2.2]octane;
1-methyl-3-[5-(2-aminoethyl)-1,2,4-oxadiazol-3-yl]indole;
1-methyl-3-[5-(2-N-methylaminoethyl)-1,2,4-oxadiazol-3-yl]indole;
1-methyl-3-[5-(2-(1-piperidyl)ethyl)-1,2,4-oxadiazol-3-yl]indole;
3-[3-(1-methylindol-2-yl)-1,2,4-oxadiazol-5-yl]-1-azabicyclo[2.2.2]octane;
6-[3-(1-methylindol-3-yl)-1,2,4-oxadiazol-5-yl]-2-azabicyclo[2.2.2]octane;
2-methyl-6-[3-(1-methylindol-3-yl)-1,2,4-oxadiazol-5-yl]-2-azabicyclo[2.2.2]octane;
3-[3-(1-methylindol-3-yl)-1,2,4-oxadiazol-5-yl]-1-azabicyclo[2.2.1]heptane;
3-[3-(1-methylindol-3-yl)-1,2,4-thiadiazol-5-yl]-1-azabicyclo[2.2.2]octane;
3-[3-(1H-indazol-3-yl)-1,2,4-oxadiazol-5-yl]-1-azabicyclo[2.2.2]octane;
3-[3-(1H-indol-3-yl)-1,2,4-oxadiazol-5-yl]-1-azabicyclo[2.2.2]octane;
3-[3-(1,7-dimethylindol-3-yl)-1,2,4-oxadiazol-5-yl]-1-azabicyclo[2.2.2]octane;
4-[2-(1-methylindol-3-yl)-1,3,4-oxadiazol-5-yl]-1-methyl-1,2,5,6-tetrahydropyridine;
3-[2-(1-methylindol-3-yl)-1,3-thiazol-4-yl]-1-methyl-1,2,5,6-tetrahydropyridine;
3-[3-(1-methylindol-3-yl)-1,2,4-thiadiazol-5-yl]-1-azabicyclo[2.2.1]heptane;
3-[3-(1H-indol-2-yl)-1,2,4-oxadiazol-5-yl]-1-azabicyclo[2.2.2]octane;
and salts and prodrugs thereof.

This invention also provides a pharmaceutical composition comprising a compound of the invention and a pharmaceutically acceptable carrier.

The compounds of the invention can be administered orally, parenterally or rectally at a daily dose of about 0.01 to 10 mg/kg of body weight, preferably about 0.1 to 1 mg/kg, and may be administered on a regimen of 1 to 4 times a day.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The oxadiazole compounds of this invention may be prepared by a process which comprises reacting a reactive derivative of a carboxylic acid of formula $R^c$—$CO_2H$ with a compound either of formula V or of formula VI, or a salt thereof:

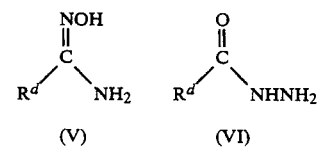

(V)            (VI)

wherein one of $R^c$ and $R^d$ is a group of formula A, and the other is a group of formula -E-F, as defined with reference to formula I above.

Suitable reactive derivatives of the acid $R^c$—$CO_2H$ include esters, for example $C_{1-4}$ alkyl esters; thioesters, for example pyridylthioesters; acid anhydrides, for example $(R^cCO)_2O$; acid halides, for example acid chlorides, orthoesters; and primary, secondary and tertiary amides.

A preferred reactive derivative of the acid $R^c$—$CO_2H$ is the iminoether derivative of formula VII:

where R is $C_{1-4}$ alkyl.

When the compound of formula V is employed the product of the reaction is a 1,2,4-oxadiazole. It will be appreciated that the compound V can also be considered as the alternative tautomeric form VA:

A 3-substituted-1,2,4-oxadiazol-5-yl compound is produced if $R^c$ represents a group -E-F and $R^d$ in formula V represents a group A; whereas a 5-substituted-1,2,4-oxadiazol-3-yl compound is produced by the process of this invention when $R^c$ represents a group A and $R^d$ represents a group -E-F. A preferred reactive derivative of the acid $R^c$—$CO_2H$ in this case is a $C_{1-4}$ alkyl ester. The reaction is conveniently carried out in tetrahydrofuran, dimethylformamide or a lower alkanol such as ethanol, propanol or isopropanol at about 20° to 100° C. for about 1 to 6 hours.

When the compound of formula VI is employed, the product of the process of this invention is a 1,3,4-oxadiazole. In this case, a preferred reactive derivative of the acid $R^c$—$CO_2H$ is an orthoester of formula $R^cC(OR^p)_3$ where $R^p$ represents $C_{1-3}$ alkyl. The process is conveniently effected by heating the hydrazide VI with the orthoester in a solvent such as methanol at reflux temperature for about 2 to 8 hours. An intermediate of formula $R^d.CO.NH.N=C(R^c)OR^p$ may be isolated by evaporation of the solvent. The intermediate is then treated with a strong base such as potassium t-butoxide or 1,8-diazabicyclo[5.4.0]undec-7-ene, in butanol for about 10 to 24 hours at about 90° to 150° C.

The 1,2,4-thiadiazoles of formula I may be prepared by a process which comprises the cyclisation of a compound of formula VIII:

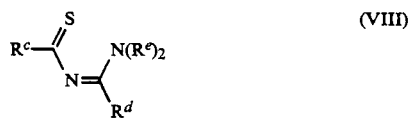

wherein $R^c$ and $R^d$ are as defined above, and $R^e$ is hydrogen or an alkyl group.

Cyclisation of compound VIII can be achieved using an aminating agent such as hydroxylamine-O-sulphonic acid in a lower alkanol such as methanol, ethanol or propanol, in the presence of pyridine, at between −20° C. and 50° C. for about 1-6 hours.

Cyclisation of compounds of formula VIII in which $R^e$ is hydrogen may also be achieved by use of an oxidising agent such as bromine, iodine, hydrogen peroxide or nitric acid.

The 1,2,4-thiadiazoles may also be prepared by cycloaddition of a nitrile sulphide $R^c$—$C\equiv N^+$—$S^-$ with a nitrile of formula $R^dCN$ where $R^c$ and $R^d$ are as defined above.

A further method for the preparation of the 1,2,4-thiadiazoles of this invention comprises reaction of a thiadiazole of formula IX:

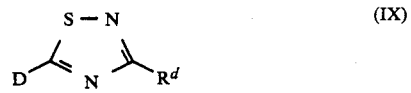

with a reagent which provides an anion $^-R^c$, where $R^c$ and $R^d$ are as previously defined and D represents halogen. Compound IX may be prepared by the general method described in Chem. Ber., 1957, 90, 182.

Reagents which may provide the anion $^-R^c$ include Grignard reagents $R^cMgHal$ (where Hal=halogen); organocuprate reagents such as $LiR^c_2Cu$; organolithium reagents $R^cLi$; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated. moiety may be hydrolysed and decarboxylated.

1,3,4-Thiadiazoles of this invention may be prepared by dehydration of a thiosemicarbazide of formula $R^cCSNHNHCONR^sR^t$, where $R^c$ is as defined above and $R^s$ and $R^t$ are hydrogen or an alkyl group, with a dehydrating agent such as sulphuric acid, polyphosphoric acid or methanesulphonic acid; followed by attachment of the $R^d$ group by conventional means.

The oxazoles and thiazoles of this invention may be prepared by reaction of an amide or thioamide of formula X with a α-haloketone of formula XI:

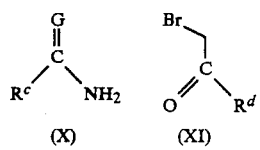

wherein G is oxygen or sulphur, and $R^c$ and $R^d$ are as defined above. The conditions for this reaction are as described in Synthesis, 1975, 389.

The imidazoles of this invention may be prepared by conventional methods, such as are described in Advances in Heterocyclic Chemistry, 1970, 12, 104. One suitable process may be illustrated as follows:

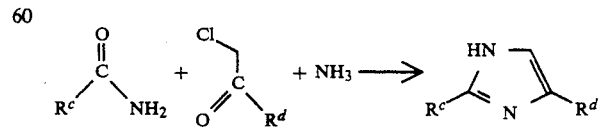

The oxazoline and thiazoline compounds of this invention may be prepared by a process which comprises reacting a reactive derivative of a carboxylic acid of formula $R^c$—$CO_2H$ with a compound either of formula XII or of formula XIII or a salt thereof:

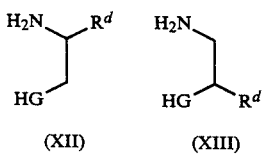

wherein G is oxygen or sulphur and $R^c$ and $R^d$ are as defined above.

The process is conveniently effected by condensation of the starting materials in the presence of thionyl chloride, phosphorus oxychloride or triphenylphosphine/-diethyl azodicarboxylate.

The intermediate of formula XIII may be prepared by conventional methods, for example:

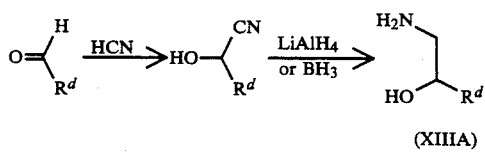

The isoxazoline compounds of this invention may be prepared by reacting a nitrile oxide with an appropriate alkene.

The furans according to the invention may, for example, be prepared by reacting a compound of formula XIV:

with a reagent which provides an anion $^-R^c$, wherein $R^c$ and $R^d$ are as previously defined; and wherein the reagent which may provide the anion $^-R^c$ is suitably as described with reference to formula IX above.

The intermediate of formula XIV may be prepared by conventional methods, for example:

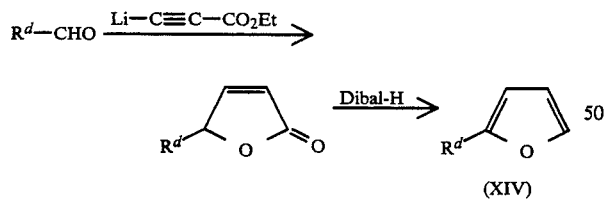

The azacyclic or azabicyclic moiety may be introduced into the molecules concerned by methods known from the art, in particular by methods analogous to those described in EP-A No. 0239309.

After any of the above described processes is complete, one substituent can be converted to another. For example an amino group may be converted to chloro, or hydrazo, —$NHNH_2$, via the intermediacy of diazonium, —$N_2$. Similarly, a chloro substituent may be converted to methoxy by reaction with a nucleophile such as methoxide; alkoxycarbonyl groups may be converted, via carboxy, to an amino substituent, —$NH_2$; and methoxy may be converted to hydroxy by treatment with concentrated hydrobromic acid.

In any of the above reactions it may be necessary and/or desirable to protect any sensitive groups in the compounds. For example, if $R^c$ and/or $R^d$ include amino, carboxy, keto, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Keto groups may be protected in the form of a ketal. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention.

The compounds according to the present invention may be evaluated for their anti-emetic activity in the von Bezold-Jarisch test (Nature, 1985, 316, 126), or in animal models of anxiety (see, for example, Br. J. Pharmac., 1988, 93, 985), schizophrenia (see, for example, Eur. J. Pharmac., 1987, 138, 303) or cognition (passive avoidance assay).

Certain of the compounds of the present invention act on 5-$HT_3$ receptors and this may account, in whole or in part, for the pharmacological activity of these compounds. The 5-$HT_3$ binding of the compounds of the invention was assayed using the protocol described in the literature (Nature, 1987, 330, 716) but instead of using the compound GR-65630 described therein, the $^3H$ methylated quaternary derivative of formula XV was employed as a radioligand:

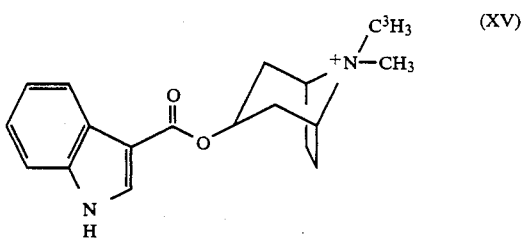

The compounds of each of the Examples demonstrate an affinity for the 5-$HT_3$ receptor with a $K_i$ (dissociation constant for the displacement of radioligand) better than 100 nM.

EXAMPLE 1

3[3-(Methylindol-3-yl)-1,2,4-oxadiazol-5-yl]-1-azabicyclo[2.2.2]octane hydrogen oxalate (a) [1-Methylindol-3-yl]amide oxime A solution of hydroxylamine hydrochloride (1.3 g), potassium carbonate (3.5 g), and 1-methylindole-3-nitrile (2 g) in absolute ethanol (100 ml) was heated under reflux for eight hours. The solvent was removed at reduced pressure and the residue extracted with ether (2×100 ml), the solvent evaporated at reduced pressure and the residue purified by recrystalisation from $CH_2Cl_2$/Acetone to afford [1-methylindol-3-yl]amide oxime as a white solid (2.9 g). mp 110° C. (dec); $\delta_H$ (360 MHz, CDCl$_3$), 3.6 (3H, s, NMe), 6.8–7.0 (2H, m, H-5, H-6), 7.11 (1H, d, J=8, H-7), 7.20 (1H, s, H-2), 7.90 (1H, d, J=8, H-4); M/Z 173 (25%), 158 (40), 156 (100), 114 (20).

(b)
3[3-(1-Methylindol-3-yl)-1,2,4-oxadiazol-5-yl]-1-azabicyclo[2.2.2]octane hydrogen oxalate The 1-methylindol-3-yl amide oxime (0.94 g) was dissolved in anhydrous DMF (30 ml) to which was added 4A molecular sieves (2 g). After stirring for 15 mins sodium hydride (0.18 g of 80% dispersion in oil) was added and the mixture stirred for a further 15 mins before the addition of 3-carbomethoxy-1-azabicyclo[2.2.2]octane (1.2 g). The resulting mixture was then warmed to 100° C. for 1 h then cooled to room temperature filtered and the solvent evaporated. The residue was then purified by chromatography on alumina using CH$_2$Cl$_2$/MeOH as eluant, to afford a colourless oil (0.9 g). This was further purified by treatment with a solution of oxalic acid in ether to afford the title compound mp 163° C. (Acetone); (Found: C, 55.34; H, 5.17; N, 12.08; C$_{20}$H$_{22}$N$_4$O$_5$ requires C, 55.74; H, 5.34; N, 12.38%; $\delta_H$ (360 MHz, D$_2$O) 1.78–2.08 (6H, m, 3×CH$_2$), 2.55 (1H, bm, CH), 3.29–3.39 (4H, m, 2×CH$_2$N), 3.66–3.88 (3H, m, CH$_2$N, —CH—), 3.88 (3H, s, NMe), 7.25–7.33 (2H, m, H-5, H-6), 7.58 (1H, d, J=8, H-7), 8.05 (1H, d, J=8, H-4), 8.16 (1H, s, H-2); M/Z 308 (M+ free base 1.5%) 225 (10), 154 (45), 91 (100).

EXAMPLE 2

2[3-(1-Methylindol-3-yl)-1,2,4-oxadiazol-5-yl]-1-azabicyclo[2.2.2]octane hydrogen oxalate This was prepared from 1-methylindol-3-yl amide oxime (0.94 g) and 2-carbomethoxy-1-azabicyclo[2.2.2]octane (1.2 g) using method described in example 1. This was purified by chromatography on silica eluting with (99:1→90:10) CH$_2$Cl$_2$/Acetone to afford a colourless oil (1.0 g). Preparation of the oxalate as described previously gave the title compound as white crystals mp 210° C.; Found C, 59.89; H, 5.65; N, 13.90 C$_{20}$H$_{22}$N$_4$O$_5$ requires C, 60.02; H, 5.59; N, 13.99%; $\delta_H$ (360 MHz, D$_2$O) 1.8–2.6 (9H, m, 3×CH$_2$), 2.5 (1H, bs, CH), 3.27–3.47 (4H, m, 2×CH$_2$N), 3.90 (3H, s, NMe), 5.12 (1H, t, J=8, CHN), 7.26–7.36 (2H, m, H-5, H-6) 7.60 (1H, d, J=8, H-7), 8.04 (1H, d, J=8, H-4), 8.15 (1H, s, H-2); M/Z 308 (M+ free base, 25%) 156 (30), 155 (100).

EXAMPLE 3

1-Methyl-3-[5-dimethylaminomethyl-1,2,4-oxadiazol-3-yl]indole hydrochloride

[1-Methylindol-3-yl]amide oxime (0.9 g,) was dissolved in anhydrous THF (30 ml) containing 4A molecular sieves (2 g) under nitrogen. After stirring for 30 mins sodium hydride (0.10 g of a 80% dispersion in oil) was added and the mixture stirred for a durther 15 mins. A solution of ethyl N,N-dimethylamino glycine (1.31 g,) in THF (10 ml) was added and the mixture heated at reflux for one hour. The reaction mixture was then cooled to room temperature, filtered and the solvent evaporated at reduced pressure. The residue was purified by chromatography on silica using CH$_2$Cl$_2$/Acetone as eluant to afford a colourless oil (0.7 g).

A sample (300 mg) was dissolved in ether (5 ml) and a solution of ethanolic HCl added, the precipitate was recrystallised from acetone to afford the title compound as a pale cream solid mp 197° C.; Found C, 57.39; H, 5.84; N, 19.00 C$_{14}$H$_{17}$N$_4$O$_4$Cl requires C, 57.43; H, 5.85; N, 19.14%; $\delta_H$ (360 MHz) 3.13 (6H, s, NMe$_2$), 3.75 (3H, s, NMe) 4.79 (2H, s, CH$_2$N), 7.29 (2H, m, H-5, H-6), 7.47 (1H, d, J=8, H-7) 7.73 (1H, s, H-2), 7.87 (1H, d, J=8, H-4); M/Z 256 (60%), 213 (55), 171 (100), 156 (70).

EXAMPLE 4

[3-(1-methylindol-3-yl)-1,2,4-oxadiazol-5-yl]methyl-trimethylammonium iodide

Methyl iodide (164 mg,) was added to a stirred solution of 1-methyl-3[3-(5-dimethylaminomethyl-1,2,4-oxadiazoyl)]indole (300 mg,) in an anhydrous acetone (30 ml). After stirring at room temperature for two hours the precipitate was isolated by filtration and dried to afford the title compound as a white solid (400 mg,) mp 218° C. (dec); Found C, 45.15; H, 4.77; N, 13.89 C$_{15}$H$_{19}$N$_4$OI requires C, 45.24; H, 4.80; N, 14.06%; $\delta_H$ (360 MHz) 3.32 (9H, s, N+Me$_3$), 3.93 (3H, s, NMe), 5.11 (3H, s, CH$_2$N+), 7.25–7.35 (2H, m, H-5, H-6), 7.80 (1H, d, J=8, H-7), 8.03 (1H, d, J=8, H-4), 8.22 (1H, s, H-2); M/Z 259 (20%), 216 (30), 214 (55), 139 (100).

EXAMPLE 5

1-methyl-4[3-(Methylindol-3-yl)-1,2,4-oxadiazol-5-yl]piperidine hydrogen oxalate This was prepared from 1-methylindol-3-yl amide oxime (0.94 g) and methyl 1-methylpiperidine-4-carboxylate (2 g) using the method described in Example 3. This was purified on alumina eluting with (2:1→1:1) CH$_2$Cl$_2$/Ethyl acetate to afford a colourless oil (1.4 g). Preparation of the oxalate as described previously gave the title compound as white crystals, mp 198° C.; Found C, 59.00; H, 5.63; N, 14.35 C$_{19}$H$_{22}$N$_4$O$_5$ requires C, 59.00; H, 5.74; N, 14.49%; $\delta_H$ (360 MHz, DMSO) 2.08–2.33 (4H, m, 2×CH$_2$), 2.76 (3H, s, Me), 3.11 (2H, brt, J=11, CH$_2$N), 3.37–3.50 (3H, m, —CH$_2$N and —CH), 3.89 (3H, s, NMe), 7.22–7.32 (2H, m, H-5, H-6), 7.57 (1H, d, J=6, H-7), 8.03 (1H, d, J=6, H-4), 8.14 (1H, s, H-2); M/Z 296 (M+ free base, 10%), 196(10), 152(35), 123(50), 96(100), 90(70).

EXAMPLE 6

1,1-Dimethyl-4-[3-(methylindol-3-yl)-1,2,4-oxadiazol-5-yl]piperidinium iodide

Methyl iodide (200 mg) was added to a stirred solution of 1-methyl-4-[3-(methylindol-3-yl)-1,2,4-oxadiazol-5-yl]piperidine (300 mg) in anhydrous acetone (20 ml) at room temperature. After stirring at room temperature for two hours the precipitate was isolated by filtration and dried to afford the title compound (300 mg), mp 246° C.; Found C, 49.00; H, 5.30; N, 12.51 C$_{18}$H$_{23}$N$_4$OI requires C, 49.32; H, 5.29; N, 12.78%; $\delta_H$ (360 MHz, DMSO) 2.25–2.35 (4H, m, 2×CH$_2$), 3.14 (3H, s, NMe), 3.18 (3H, s, NMe), 3.41 (1H, m, CH), 3.48–3.56 (4H, m, 2×CH$_2$N), 3.90 (3H, s, NMe), 7.22–7.33 (2H, m, H-5, H-6), 7.58 (1H, d, J=7, H-7), 8.05 (1H, d, J=7, H-4), 8.12 (1H, s, H-2); M/Z (no M+), 199(90), 140(100), 96(90).

EXAMPLE 7

1-Methyl-3-[3-(methylindol-3-yl)-1,2,4-oxadiazol-5-yl]piperidine hydrogen oxalate This was prepared from 1-methylindol-3-yl amide oxime (0.94 g) and methyl 1-methylpiperidine-3-carboxylate (2 g) using the method described in Example 3. This was purified on alumina eluting with (2:1→1:1) $CH_2Cl_2$/Ethyl acetate to afford a colourless oil (1.4 g). Preparation of the oxalate as described previously gave the title compound as white crystals, mp 217° C.; Found C, 60.10; H, 5.59; N, 14.15, $C_{19}H_{22}N_4O_5$ requires C, 59.06; H, 5.74; N, 14.49%; $\delta_H$ (360 MHz, DMSO) 1.74–2.41 (4H, m, 2×$CH_2$), 2.77 (3H, s, Me), 2.89 (1H, m, CH), 3.19–3.74 (4H, m, CH), 3.19–3.74 (4H, m, $CH_2N$), 3.90 (3H, s, NMe), 7.22–7.33 (2H, m, H-5, H-6), 7.57 (1H, d, J=7, H-7), 8.04 (1H, d, J=7, H-4), 8.19 (1H, s, H-2); M/Z 296 ($M^+$, free base, 10%), 185(60), 168(32), 142(45), 126(90), 82(100).

EXAMPLE 8

1,1-Dimethyl-3-[3-(Methylindol-3-yl)-1,2,4-oxadiazol-5-yl]piperidinium iodide Methyl iodide (200 mg) was added to a stirred solution of 1-methyl-3-[3-(methylindol-3-yl)-1,2,4-oxadiazol-5-yl]piperidine (300 mg) in anhydrous acetone (20 ml) at room temperature. After stirring at room temperature for two hours the precipitate was isolated by filtration and dried to afford the title compound (300 mg), mp 250° C.; Found C, 49.09; H, 5.34; N, 12.43, $C_{18}H_{23}N_4OI$ requires C, 49.32; H, 5.29; N, 12.78%; $\delta_H$ (360 MHz, DMSO), 1.68–2.18 (4H, m, 2×$CH_2$), 3.21 (3H, s, NMe), 3.24 (3H, s, NMe), 3.40–4.06 (5H, m, 2×$CH_2$, CH), 3.94 (3H, s, NMe), 7.23–7.34 (2H, m, H-5, H-6), 7.58 (1H, d, J=7, H-7), 8.04 (1H, d, J=7, H-4), 8.10 (1H, s, H-2); M/Z 311(100), 185(30), 93(59).

EXAMPLE 9

1-Methyl-3-[5-aminomethyl-1,2,4-oxadiazol-3-yl]indole hydrogen triflouroacetate (a)

1-Methyl-3-[5-t-butoxycarbonylaminomethyl-1,2,4-oxadiazol-3-yl]indole

This was prepared from 1-methylindol-3-yl amide oxime (0.94 g) and ethyl N-t-butoxycarbonyl glycinate (2 g) using the method described in Example 3. This was purified on silica eluting with $CH_2Cl_2$ to afford a pale yellow solid (1.4 g) mp 150° C.; $\delta_H$ (360 MHz, CDCl$_3$) 1.48 (9H, s, t-Bu), 3.83 (3H, s, NMe), 4.6 (2H, brs, $CH_2N$), 5.28 (1H, brs, NH), 7.25–7.37 (3H, m, H-5, H-6, H-7), 7.76 (1H, s, H-2), 8.20 (1H, d, J=7, H-4); M/Z 328 ($M^+$, 60%), 272(40), 228(25), 156(100).

(b)

1-Methyl-3-[5-aminomethyl-1,2,4-oxadiazol-3-yl]indole hydrogen triflourocetate

1-Methyl-3-[5-t-butoxycarbonylaminomethyl-1,2,4-oxadiazol-3-yl]indole (300 mg) was dissolved in $CH_2Cl_2$ (10 ml) at 0° C., trifluoroacetic acid (0.5 ml) was then added and the reaction mixture allowed to warm to room temperature over 30 mins. The reaction mixture was stirred at room temperature for twelve hours before evaporation at reduced pressure. The residue was recrystallised from cold $CH_2Cl_2$ to afford white crystals (150 mg) mp 178° C.; Found C, 48.74; H, 3.74; N, 15.97 $C_{14}H_{13}N_4O_3F_3$ requires C, 49.13; H, 3.83; N, 16.37%; $\delta_H$ (360 MHz, DMSO), 3.92 (3H, s, NMe), 4.58 (2H, s, $CH_2N$), 7.24–7.35 (2H, m, H-5, H-6), 7.60 (1H, d, J=7, H-4), 8.07 (1H, d, J=7, H-7), 8.10 (1H, s, H-2); M/Z 228 ($M^+$, free base 70%), 171(100), 156(80).

EXAMPLE 10

1-Methyl-3-[5-methylaminomethyl-1,2,4-oxadiazol-3-yl]indole hydrogen trifluoracetate (a)

1-Methyl-3-[5-t-butoxycarbonyl-N-methylaminomethyl-1,2,4-oxadiazol-3-yl]indole

1-Methyl-3-[5-t-butoxycarbonylaminomethyl-1,2,4-oxadiazol-3-yl]indole (300 mg) was dissolved in anhydrous tetrahydrofuran (10 ml) and cooled to 0° C. under nitrogen. Sodium hydride (0.1 g) was added followed by methyl iodide (0.2 ml) and the mixture allowed to warm to room temperature. The mixture was stirred at room temperature for 30 mins then diluted with ether (20 ml) and washed with water (10 ml), dried ($Na_2SO_4$) and the solvent evaporated. The residue was purified by chromatography on silica eluting with $CH_2Cl_2$ to afford a colourless oil (300 mg); $\delta_H$ (360 MHz, CDCl$_3$), 1.43 (9H, brs, t-But), 3.09 (3H, brs, $CH_3$), 3.86 (3H, s, NMe), 4.6 (2H, brs, $CH_2N$), 7.25–7.39 (3H, m, H-5, H-6, H-7), 7.79 (1H, s, H-2), 8.22 (1H, d, J=7, H-4).

(b)

1-Methyl-3-[5-methylaminomethyl-1,2,4-oxadiazol-3-yl]indole hydrogen trifluoracetate Using the procedure described in Example 7, 1-methyl-3-[5-t-butoxycarbonyl-N-methylaminomethyl-1,2,4-oxadiazol-3-yl]indole (300 mg) afforded the title compound as white crystals (170 mg) mp 195° C.; Found C, 50.37; H, 4.28; N, 15.37 $C_{15}H_{15}F_3N_4O_3$ requires C, 50.56; H, 4.24; N, 15.72%; $\delta_H$ (360 MHz, DMSO) 2.80 (3H, s, $CH_3$), 3.92 (3H, s, NMe), 4.71 (2H, s, $CH_2$), 7.25–7.35 (2H, m, H-5, H-6), 7.60 (1H, d, J=7, H-7), 8.07 (1H, d, J=7, H-4), 8.13 (1H, s, H-2); M/Z 242 ($M^+$, free base, 90%), 171(100), 156(80).

EXAMPLE 11

1-Methyl-3-[5-dimethylaminoethyl-1,2,4-oxadiazol-3-yl]indole hydrogen oxalate hydrate This was prepared from 1-methylindol-3-yl amide oxime (0.94 g) and methyl 3-dimethylaminopropanoate (1.31 g) using the method described in Example 3. This was purified on alumina eluting with (1:0–7:3) CHCl$_3$/Ethyl acetate to afford a pale yellow oil (0.7 g). Preparation of the oxalate as described previously gave the title compound as white crystals, mp 186° C.; Found C, 56.22; H, 5.63; N, 15.18 $C_{17}H_{20}N_4O_5$, 0.2$H_2O$ requires C, 56.66; H, 5.59; N, 15.54%; $\delta_H$ (360 MHz, dmso), 2.78 (6H, s, 2×$NCH_3$), 3.44–3.52 (2H, m, $CH_2$), 3.91 (3H, s, NMe), 7.23–7.34 (2H, m, H-5, H-6), 7.58 (2H, d, J=8 Hz, H-7), 8.05 (1H, d, J=8 Hz, H-4), 8.14 (1H, s, H-2); m/z 270 ($M^+$, free base, 20%) 182 (35), 156 (100), 155 (45), 129 (35).

EXAMPLE 12

3-[3-(Methylindol-3-yl)-1,2,4-oxadiazol-5-yl]-8-methyl-8-azabicyclo[3.2.1]octane hydrogen oxalate This was prepared from 1-methylindol-3-yl amide oxime (0.94 g) and 3-carbomethoxy-8-methyl-8-azabicyclo[3.2.1]octane (0.7 g) using the method described in Example 3. This was purified on alumina eluting with (99:1–95:5) $CH_2Cl_2$/methanol to afford a colourless oil (0.4 g). Preparation of the oxalate as described previously gave the title compound as white crystals, mp 209° C.; Found C, 60.57; H, 5.95; N, 12.70 $C_{21}H_{24}N_4O_5$ requires C, 60.61; H, 6.18; N, 12.72%; $\delta_H$ (360 MHz, DMSO), 2.1–2.45 (8H, m, 4×$CH_2$), 2.80 (3H, s, NMe), 3.44 (1H, m, CH), 3.74 (3H, s, NMe), 4.07 (2H, m, 2×CHN), 7.27–7.38 (2H, m, H-5, H-6), 7.46 (1H, d, J=8 Hz, H-7), 7.60 (1H, s, H-2), 7.28 (1H, d, J=8 Hz, H-4); m/z 156 (35), 124 (20), 82 (50), 28 (100).

EXAMPLE 13

3-[3-Methylindol-3-yl)-3-yl)-1,2,4-oxadiazol-5-yl]-1,2,5,6-tetrahydropyridine hydrogen trifluoracetate (a)

3-[3-Methylindol-3-yl)-1,2,4-oxadiazol-5-yl]-1-t-butoxycarbonyl-1,2,5,6-tetrahydropyridine This was prepared from 1-methylindol-3-yl amide oxime (0.94 g) and methyl 1-t-butoxycarbonyl-1,2,5,6-tetrahydropyridine-3-carboxylate (1.2 g) using the method described in Example 3. This was purified by recrystallisation from $CHCl_3$ to afford a pale yellow solid (600 mg) mp 170° C.; $\delta_H$(CDCl_3, 360 MHz), 1.51 (9H, s, t-Bu), 2.44 (2H, m, $CH_2$), 3.6 (2H, m, $CN_2N$), 3.87 (3H, s, NMe), 4.43 (2H, m, $CH_2N$), 7.2 (1H, brs, NH), 7.26–7.39 (4H, m, H-5, H-6, h-7, =CH—), 7.82 (1H, s, H-2), 8.24 (1H, d, J=8, H-4); m/z 367 (10), 311 (60), 158 (25), 115 (35), 73 (100).

(b)

3-[3-Methylindol-3-yl)-1,2,4-oxadiazol-5-yl]-1,2,5,6-tetrahydropyridine hydrogen trifluoroacetate Trifluoroacetic acid (1 ml) was added dropwise to a stirred solution of 3-[3-methylindol-3-yl)-1,2,4-oxadiazol-5-yl]-1-t-butoxycarbonyl-1,2,5,6-tetrahydropyridine (0.3 g) in dichloromethane (10 ml). The resulting mixture was stirred at room temperature for 24 hr then the solvent removed at reduced pressure. The residue was recrystallised from chloroform to afford the title compound (200 mg) as a pale yellow solid, mp 167° C.; Found C, 54.51; H, 4.10; N, 14.31; $C_{18}H_{17}F_3N_4O_3$ requires C, 54.82; H, 4.34; N, 14.21%; $\delta_H$ (360 MHz, DMSO) 2.63 (2H, m, $CH_2$), 3.32 (2H, m, $CH_2N$), 3.91 (3H, s, NMe), 4.14 (2H, m, $CH_2N$), 7.21–7.34 (3H, m, H-5, H-6, =CH—), 7.58 (1H, d, J=8 Hz, H-7), 8.05 (1H, d, J=8 Hz, H-5), 8.15 (1H, s, H-2); m/z 280 ($M^+$, free base, 100%), 171 (45), 156 (40), 81 (50), 59 (75).

EXAMPLE 14

3-[3-(Methylindol-3-yl)-1,2,4-oxadiazol-5-yl]-1-methyl-1,2,5,6-tetrahydropyridine hydrogen oxalate This was prepared from 1-methylindol-3-yl amide oxime (0.94 g) and ethyl 1-methyl-1,2,5,6-tetrahydropyridine-3-carboxylate (1.2 g) using the procedure described in Example 3. This was purified on alumina eluting with $CH_2Cl_2$ to afford a white solid (300 mg) mp 120° C. Preparation of the oxalate as described previously gave the title compound as a white solid (300 mg) mp 232° C.; Found C, 59.26; H, 5.05; N, 14.50 $C_{19}H_{20}N_4O_5$ requires C, 59.36; H, 5.24, N, 14.57%; $\delta_H$ (360 MHz, DMSO) 2.69 (2H, m, $CH_2$), 2.88 (3H, s, NMe), 3.28 (2H, m, $CH_2N$), 3.90 (3H, m, $NCH_3$), 4.12 (2H, m, $CH_2N$), 7.23–7.34 (3H, m, H-5, H-6, =CH—), 7.58 (1H, d, J=8 Hz, H-7), 8.06 (1H, d, J=8 Hz, H-4), 8.14 (1H, s, H-2); m/z 294 ($M^+$, free base, 70%), 251 (100), 156 (50), 81 (30).

EXAMPLE 15

3-[5-(1-Methylindol-3-yl)-1,2,4-oxadiazol-3-yl]-1-azabicyclo[2.2.2]octane sesqui hydrogen oxalate The azabicyclo[2.2.2]octan-3-yl-carboxamide oxime (prepared using the method described in EP No. 239309A) was dissolved in anhydrous THF (30 ml) and anhydrous DMF (20 ml) to which was added 4A molecular sieves (0.8 g). After stirring for 15 mins sodium hydride (0.14 g of 80% dispersion in oil) was added and the mixture stirred for a further 15 mins before the addition of 1-methylindol-3-yl carboxylate methyl ester (1.7 g). The resulting mixture was heated at reflux for 4 hours, then cooled, filtered through hyflo and the solvent evaporated. The residue was purified by chromatography on alumina using MeOH/EtOAc as eluant to give a white solid (0.5 g). The title compound was isolated by dissolution of the free base (150 mg) in hot MeOH (4 ml) followed by treatment with a solution of oxalic acid in ether whereupon the salt crystallised on standing as a white crystalline solid (140 mg) mp 170°–171° C. (MeOH). Found: C, 56.89; H, 5.30; N, 12.76; $C_{21}H_{23}N_4O_7$ requires C, 56.88; H, 5.23; N, 12.63%; $\delta_H$ (360 MHz, DMSO-d_6) 1.1–2.1 (4H, m, 2×$CH_2$), 2.50 (1H, m, CH), 3.2–3.4 (4H, brm, 2×$CH_2N$), 3.60–3.75 (3H, m, $CH_2N$, —CH—), 3.94 (3H, s, NMe), 7.31–7.39 (2H, m, H-5, H-6), 7.64 (1H, d, J=7 Hz, H-7), 8.11 (1H, dd, J=7 Hz, H-4), 8.44 (1H, s, H-2); m/z ($CI^+$) 308 ($M^+$ free base, 30%) 225 (40), 158 (100), 130 (15).

EXAMPLE 16

3-[3-(5-Fluoro-1-methylindol-3-yl)-1,2,4-oxadiazol-5-yl]-1-azabicyclo[2.2.2]octane hydrogen oxalate (a) [5-Fluoro-1-methylindol-3-yl]amide oxime This was prepared from 3-cyano-5-fluoro-1-methylindole (3 g), hydroxylamine hydrochloride (1.8 g) and potassium carbonate (4.7 g) using the method described in Example 1. Recrystallisation from $CH_2Cl_2$/acetone afforded [5-fluoro-1-methylindol-3-yl]amide oxime as a pale yellow solid (1 g); m.p. 115° C.; $\delta_H$ (360 MHz, DMSO-d_6) 3.39 (3H, s, NMe), 6.55 (1H, m, H-6), 6.82 (1H, m, H-4), 7.28 (1H, s, H-2), 7.39 (1H, d, J=7 Hz, H-7); m/z 207 ($M^+$, 55%), 191 (45), 175 (100), 160 (43), 147 (65).

(b)

3-[(5-Fluoro-1-methylindol-3-yl)-1,2,4-oxadiazol-5-yl]-1-azabicyclo[2.2.2]octane dihydrogen oxalate This was prepared from [5-fluoro-1-methylindol-3-yl]amide oxime (0.7 g) and 3-carbomethoxy-1-azabicyclo[2.2.2]octane (1.1 g) using the method described in Example 1. This was purified on alumina eluting with (99:1→90:10) $CH_2Cl_2$/MeOH to afford a colourless oil (400 mg). Preparation of the oxalate as described previously gave the title compound as white crystals, m.p. 188° C. Found: C, 54.23; H, 4.92; N, 11.63. $C_{20}H_{20}FN_4O_5$ requires C, 53.99; H, 4.53; N, 11.45%; $\delta_H$ (360 MHz, $D_2O$) 1.9–2.2 (4H, m, 2×$CH_2$), 2.67 (1H, brs, CH), 3.35–3.52 (4H, m, 2×$CH_2N$), 3.67 (3H, s, NMe), 3.80–3.91 (3H, m, $CH_2N$, CH), 7.02 (1H, m, H-6), 7.29–7.34 (2H, m, H-4, H-7), 7.59 (1H, s, H-2); m/z No $M^+$, 233(20%), 167(50), 91(100).

EXAMPLE 17

3-[4-(5-Cyanoindol-3-yl)-1,3-thiazol-2-yl]-1-methyl-1,2,5,6-tetrahydropyridine hydrogen oxalate (a) 3-[2-(5-Cyanoindol-3-yl)-1,3-thiazol-4-yl]-pyridine A solution of thionicotinamide (2.76 g), and 3-bromoacetyl-5-cyanoindole (5.26 g) in dimethyformamide (100 ml) were heated at reflux under nitrogen for 3 hours. The mixture was cooled to room temperature and poured into 3% aqueous sodium bicarbonate solution (300 ml). The product was then isolated by filtration, washed with water (100 ml) and dried over $P_2O_5$ to afford a buff coloured solid (4.8 g), m.p. 240° C.; $\delta_H$ (360 MHz, DMSO-$d_6$) 7.55–7.64 (3H, m, H-6, H-7, β-pyr), 8.13 (1H, s, CH), 8.22 (1H, d, J=1 Hz, H-4), 8.43 (1H, m, γ-pyr), 8.74 (2H, m, α-pyr), 9.27 (1H, s, H-2), 12.03 (1H, s, NH); m/z 302 (M+, 35%), 256 (15), 198 (30).

(b) 3-[4-(5-Cyanoindol-3-yl)-1,3-thiazol-2-yl]-1-methyl pyridinium iodide

A solution of 3-[2-(5-cyanoindol-3-yl)-1,3-thiazol-4-yl]-pyridine (2 g) and methyl iodide (1 ml) in dry acetone (200 ml) was heated at reflux for 11 hours; the mixture was then cooled and the product isolated by filtration, m.p. 285° C. (dec); $\delta_H$ (360 MHz, DMSO-$d_6$) 4.51 (3H, s, Me), 7.49–7.59 (2H, m, H-6, H-7), 8.27–8.33 (2H, 2×d, J=6, α-pyr, γ-pyr), 9.70 (1H, s, α-pyr), 12.09 (1H, s, NH); m/z 428 (10%), 308 (100), 225 (63), 142 (70).

(c) 3-[4-(5-Cyanoindol-3-yl)-1,3-thiazol-2-yl]-1-methyl-1,2,5,6-tetrahydropyridine hydrogen oxalate To a suspension of 3-[4-(5-cyanoindol-3-yl)-1,3-thiazol-2-yl]-1-methylpyridinium iodide (2.3 g) in ethanol (50 ml) and water (5 ml) was added sodium borohydride (300 mg) with vigorous stirring. After complete reaction (2 hours) 5N hydrochloric acid was added dropwise to decompose excess $NaBH_4$. The solution was then poured into 5% aqueous sodium bicarbonate (200 ml) and extracted with dichloromethane (3×100 ml), dried ($Na_2SO_4$) and evaporated. The residue was purified by chromatography on alumina eluting with $CH_2Cl_2$/MeOH (100%→90:10) to afford a pale yellow solid, (1.0 g) m.p. 217° C. This was further purified by preparation of the oxalate to yield the title compound (1.1 g), m.p. 247° C. Found: C, 58.19; H, 4.53; N, 13.39; $C_{22}H_{12}N_4O_4S$ requires C, 58.52; H, 4.42; N, 13.65%; $\delta_H$ (360 MHz, $D_2O$) 2.59 (2H, m, $CH_2$), 2.87 (3H, s, NMe), 3.22 (2H, brs, $CH_2N$), 4.17 (2H, m, =$CCH_2N$), 6.61 (1H, bs, =CH), 7.50–7.65 (2H, m, H-6, H-7), 7.95 (1H, s, CH), 8.10 (1H, d, J=1 Hz, H-2), 8.62 (1H, s, H-4), 12.06 (1H, brs, NH); m/z 320 (M+free base, 100%), 276 (55) 198 (50), 109 (35).

EXAMPLE 18

3-[3-(1-Methylindol-3-yl)-1,2,4-oxadiazol-5-yl]-1-aza-2-methoxybicyclo[2.2.2]octane hydrogen sesqui oxalate This was prepared from [1-methylindol-3-yl]amide oxime (0.94 g) and 3-carbomethoxyl-1-azabicyclo[2.2.2]oct-2-ene (1.2 g) using the method described in Example 3. This was purified on alumina eluting with $CH_2Cl_2$/MeOH (100%→99:1) to afford a waxy solid m.p. 92°–95° C. This was further purified by preparation of the oxalate salt as described previously to afford a white solid, m.p. 182° C. Found: C, 55.82; H, 5.39; N, 11.76, $C_{22}H_{25}N_4O_8$ requires C, 55.81; H, 5.32; N, 11.83%; $\delta_H$ (360 MHz, $D_2O$), 1.85–2.22 (4H, m, 2×$CH_2$) 2.68 (1H, brs, CH), 3.34 (1H, m, CH), 3.47–3.63 (4H, m, 2×$CH_2N$), 3.71 (3H, s, OMe), 3.83 (3H, s, NMe), 6.37 (1H, d, J=5.2 Hz, CHOMe), 7.31–7.40 (2H, m, H-5, H-6), 7.55 (1H, d, J=6 Hz, H-7), 7.88 (1H, s, H-2), 7.97 (1H, d, J=6 Hz, H-4); m/z 338 (M+free base, 100%), 251 (53) 156 (50).

EXAMPLE 19

1-Methyl-3-[5-(2-aminoethyl)-1,2,4-oxadiazol-3-yl]indole hydrogen oxalate (a)

2[3-(1-Methylindol-3-yl)-1,2,4-oxadiazol-5-yl]-ethene

[Methylindol-3-yl]amide oxime (1.89 g and powdered molecular sieves (2 g, 4A) were suspended in anhydrous THF (40 ml) under a nitrogen atmosphere and were stirred for 30 min. NaH (0.52 g, 50% dispersion in oil) was added and the mixture was heated to 60° C. for 15 min. The mixture was cooled to room temperature and methyl acrylate (0.9 ml) added. This was stirred for 15 min at room temperature and then heated at reflux for 1 hour. The reaction was quenched with water and the solvent was removed under reduced pressure. The residue was partitioned between $CH_2Cl_2$ and water. The organic layer was separated, dried ($Na_2SO_4$) and the solvent evaporated at reduced pressure. The residue was purified by chromatography on silica using $CH_2Cl_2$ as eluant. This afforded a colourless oil which solidified upon refrigeration to a white crystalline material, 0.5 g, m.p. 54°–55° C. (ether/hexane). Found: C, 69.32; H, 5.04; N, 18.63; $C_{13}H_{11}N_3O$ requires C, 69.32; H, 4.92; N, 18.65%; $\delta_H$ (360 MHz, $CDCl_3$) 3.79 (3H, s, $NCH_3$), 5.92 (1H, dd, J=11.0, 0.7 Hz, CH=$CH_2$), 6.54 (1H, dd, J=18.0, 0.7 Hz, CH=$CH_2$), 6.74 (1H, dd, J=18.0, 11.0 Hz CH=$CH_2$), 7.26–7.34 (3H, m, H-5, H-7, ArH), 7.76 (1H, s, ArH, H-2), 8.23–8.26 (1H, m, ArH, H-4); m/z 225 (M+, 100%), 172 (40), 156 (40).

(b)

1-Methyl-3-[5-(2-aminoethyl)-1,2,4-oxadiazol-3-yl]indole hydrogen oxalate

2[3-(1-Methylindol-3-yl)-1,2,4-oxadiazol-5-yl]-ethene (0.34 g) was dissolved in ethanol (50 ml), THF (10 ml). The solution was cooled to 0° C. and ammonia bubbled through the solution for 2 h. The flask was sealed securely at 0° C. and was allowed to stir at room temperature overnight. The solvent was removed under reduced pressure to yield a pale yellow oil, 0.36 g. The crude oil was purified by treatment with one equivalent of oxalic acid in dichloromethane which precipitated the monooxalate as a white powder which was recrystallised from methanol/acetone, m.p. 140°–141° C. Found: C, 54.12; H, 5.09; N, 17.06; $C_{15}H_{16}N_4O_5$ requires C, 54.22; H, 4.85; N, 16.86%; $\delta_H$ (360 MHz, $D_2O$). 3.44 (2H, t, J=7 Hz, $CH_2CH_2NH_2$), 3.59 (2H, t, J=7 Hz, $CH_2NH_2$), 3.88 (3H, s, $CH_3$), 7.36 (1H, dt, J=7.0, 1.2 Hz, ArH), 7.43 (1H, dt, J=7, 1.2 Hz, ArH), 7.59 (1H, d, J=7.2 Hz, H-7), 7.94 (1H, s, H-2), 8.03 (1H, d, J=8.0 Hz H-4); m/z 242 (M+free base, 90%), 212 (50), 171 (100).

EXAMPLE 20

1-Methyl-3-[5-(2-N-methylaminoethyl)-1,2,4-oxadiazol-3-yl]indole hydrogen oxalate This was prepared from 2[3-(1-Methylindol-3-yl)-1,2,4-oxadiazol-5-yl]ethene and gaseous methylamine according to the procedure described in Example 19. This afforded a pale yellow oil. The crude oil was purified, as in Example 1, by treatment with a $CH_2Cl_2$ solution of oxalic acid, yielding a white microcrystalline powder, m.p. ($H_2O$) (190° C., dec); Found: C, 55.57; H, 5.39; N, 16.00; $C_{14}H_{16}N_4O$. $(COOH)_2$ requires C, 55.49; H, 5.24; N, 16.18%; $\delta_H$ (360 MHz, $D_2O$) 2.87 (3H, s, NHCH$_3$), 3.35 (2H, t, J=7.2 Hz, C$\underline{H_2}$CH$_2$N), 3.54 (2H, t, J=7.0 Hz, CH$_2$N), 3.70 (3H, s, NCH$_3$), 7.28 (1H, dt, J=6.8, 1.0 Hz, ArH), 7.36 (1H, dt, J=6.8, 1.1 Hz, ArH), 7.55 (1H, s, H-2, ArH), 7.79 (1H, d, J=7.8 Hz, H-4); m/z 256 (M+free base, 20%), 156 (90), 91 (100).

EXAMPLE 21

1-Methyl-3-[5-(2-(1-piperidyl)ethyl)-1,2,4-oxadiazol-3-yl]indole hydrogen oxalate 2[3-(1-Methylindol-3-yl)-1,2,4-oxadiazol-5-yl]ethene (0.4 g) was partially dissolved in ethanol. Piperidine (2 ml) was added to the mixture and this was stirred for 10 minutes. Ethanol was evaporated under reduced pressure and excess piperidine was removed by heating under high vacuum. The residual oil crystallised upon refrigeration. The crude oil was converted to the monooxalate salt by treatment with 1 equivalent of oxalic acid in dichloromethane which afforded a white amorphous powder. This was recrystallised from ethanol yielding the title compound, m.p. 186°–188° C. Found: C, 59.85; H, 6.10; N, 13.95; $C_{18}H_{22}N_4O$. $(COOH)_2$ requires C, 59.99; H, 6.04; N, 13.99%; $\delta_H$(360 MHz, $D_2O$) 1.48–2.06 (8H, m, $CH_2$ pip: NCH$_2$C$\underline{H_2}\times2$+NCH$_2$CH$_2$C$\underline{H_2}$), 3.00–3.08 (2H, m, NCH$_2$) 3.50 (2H, t, J=9 Hz, C$\underline{H_2}$CH$_2$N), 3.58–3.70 (4H, m, C$\underline{H_2}$CH$_2$N+NC$\underline{H_2}$CH$_2$ pip, overlapping), 3.87 (3H, s, NC$\underline{H_3}$), 7.36 (dt, 1$\overline{H}$, J=7.2, 1.1 Hz, H-5 or H-6), 7.42 (1H, d, J=7.2, 1.1 Hz, H-5 or H-6) 7.58 (1H, d, J=8.2 Hz, H-7), 7.89 (s, 1H, H-2), 8.00 (1H, d, J=7.5 Hz, H-4); m/z (CI+) 311 (M+ +1, 100%), 226 (30), 157 (70), 98 (90).

EXAMPLE 22

3[3-(1Methylindol-2-yl)-1,2,4-oxadiazol-5-yl]-1-azabicyclo[2.2.2]octane hydrogen oxalate

(a) [1-Methylindol-2-yl]amide oxime

1-Methylindol-2-nitrile (2.5 g) was heated at reflux in ethanol (50 ml) with hydroxylamine hydrochloride (1.7 g) and potassium carbonate (4.4 g) for 3 hours. The solvent was evaporated at reduced pressure and the residue triturated with ice cold water (30 ml). The crude produce was collected as an orange solid and dried in vacuo over $P_2O_5$ (2.7 g). It was found to be contaminated with 1-methylindol-2-amide (20%) but was used without further purification, m.p. 135°–139° C. (dec); $\delta_H$(250 MHz), DMSO-d$_6$) 3.90 (3H, s, NCH$_3$), 5.88 (2H, brs, NH$_2$), 6.80 (1H, s, H-3), 7.0–7.6 (4H, m, ArH); m/z 189 (M+, 8%) 172 (50).

(b) 3-[3-(1-Methylindol-2-yl)-1,2,4-oxadiazol-5-yl]-1-azabicyclo[2.2.2]octane hydrogen oxalate This was prepared from [1-methylindol-2-yl]amide oxime (0.85 g) and 3-carbomethoxy-1-azabicyclo[2.2.2]octane (1.7 g) using the method described in Example 3. This was purified by flash chromatography on silica eluting with $CH_2Cl_2$/MeOH 95:5 to afford a pinkish oil (710 mg). This was further purified by formation of the oxalate salt to afford the title compound (0.4 g), m.p. 189° C. (dec). Found: C, 60.06; H, 5.63; N, 13.98, $C_{20}H_{22}N_4O_5$ requires C, 60.29; H, 5.57; N, 14.06%; $\delta_H$ (360 MHz, $D_2O$) 1.4–1.8 (4H, m, 2×CH$_2$), 2.32 (1H, brs, CH), 2.9–3.1 (4H, m, 2×CH$_2$N), 3.32–3.37 (2H, m, CH-C$\underline{H_2}$N), 3.50 (1H, dd, J=11, 5 Hz, CH), 4.13 (3H, s, NMe), 7.14 (1H, dd, J=8, 8, H-6), 7.32 (1H, m, H-5), 7.33 (1H, s, H-2), 7.39 (1H, d, J=8, H-7), 7.68 (1H, d, J=8, H-4); m/z 308 (M+free base, 70%), 225 (100), 156 (43).

EXAMPLE 23

(1R*,6R*)6-[3-(1-Methylindol-3-yl)-1,2,4-oxadiazol-5-yl]-2-azabicyclo[2.2.2]octane hydrogen oxalate and (1R*,6S*)-6-[3-(1-Methylindol-3-yl)-1,2,4-oxadiazol-5-yl]-2-azabicyclo[2.2.2]octane hydrogen oxalate

(a) Methyl-2-t-butyloxycarbonyl-2-azabicyclo[2.2.2]octane-6-carboxylate

Di-t-butyldicarbonate (21.8 g), in dry $CH_2Cl_2$ (50 ml) was added dropwise to a stirred, cooled (0° C.) solution of methyl 2-azabicyclo[2.2.2]octane-6-carboxylate (18.2 g), (a mixture of endo and exo isomers, prepared as described in Example 21A, EP No. 0239309) in dry $CH_2Cl_2$ (100 ml). The resulting solution was stirred at room temperature for 4 hours, water (100 ml) was added and the mixture was stirred for 15 minutes. The organic layer was separated and washed with 0.5M hydrochloric acid (100 ml), water (100 ml), saturated NaHCO$_3$ solution (100 ml) then dried over $Na_2SO_2$ and evaporated to dryness. The residue was purified by column chromatography on silica by elution with ethyl acetate/petroleum ether (60–80) [1:40] to give Isomer A as a colourless oil which crystallised on standing (12.0 g), m.p. 44°–45° C. Rf=0.35 in ethyl acetate/petroleum ether (60–80) [1:1] on silica. Found: C, 62.59; H, 8.55; N, 5.10; $C_{14}H_{23}NO_4$ requires C, 62.43; H, 8.61; N, 5.20%; $v_{max}$ (film) 1740 and 1695 cm$^{-1}$ (C=O); $\delta_H$ (360 MHz, CDCl$_3$) 1.47 (9H, s, C(CH$_3$)$_3$); 1.55–2.20 (7H, m, 3×CH$_2$, CH), 2.86–3.00 (1H, m, —CH—), 3.30 (2H, brs, CH$_2$N), 3.69 and 3.72 (total 3H, 2×brs, CO$_3$CH$_3$, rotamers), 4.21 and 4.38 (total 1H, 2×brs, CHN, rotamers). Mixed fractions were collected (1:1 mixture, 4.80 g) followed by Isomer B as a colourless oil (6.8 g). Rf=0.32 in ethyl acetate/petroleum ether (60–80) [1:1] on silica; $\delta_H$(360 MHz, CDCl$_3$) 1.42 and 1.43 (total 9H, 2×s, C(CH$_3$)$_3$, rotamers), 1.52–2.20 (7H, m, 3×CH$_2$, CH), 2.63–2.73 (1H, m, —CH—), 3.19–3.25 (1H, m, CHHN), 3.36–3.42 (1H, m, CHH$\underline{N}$), 3.66 and 3.69 (total 3$\overline{H}$, 2×s, CO$_2$CH$_3$, rotamers), 4.27–4.30 and 4.36–4.38 (total 1H, 2×m, CHN, rotamers); m/z 269 (M+).

(b) (1R*,6R*) 2-t-Butyloxycarbonyl-6-[3-(1-methylindol-3-yl)-1,2,4-oxadiazol-5-yl]-2-azabicyclo[2.2.2]octane (isomer A) and (1R*,6S*) 2-t-butyloxycarbonyl-6-[3-(1-methylindol-3-yl)-1,2,4-oxadiazol-5-yl[-2-azabicyclo[2.2.2]octane (isomer B)

The [1-methylindol-3-yl]amide oxime (0.99 g) was stirred vigorously in anhydrous THF (50 ml) for 15 minutes with 4A molecular sieves (0.8 g). Sodium hydride (0.24 g of 80% dispersion in oil) was added and the mixture stirred for 30 minutes, before the addition of methyl 2-t-butyloxycarbonyl-2-azabicyclo[2.2.2]octane-6-carboxylate (0.94 g) (1:1 mixture of isomers) dissolved in THF (10 ml). The resulting mixture was heated at reflux for 20 hours, then cooled to room temperature, filtered through hyflo and the solvent evaporated. The residue was purified and the isomers separated by flash silica chromatography using 3:1 hexane/EtOAc to yield isomer A (0.20 g) as a waxy solid and isomer and B (0.44 g) as a crystalline solid. Isomer A: $\delta_H$ (360 MHz, CDCl$_3$) 1.50 (9H, s, C(CH$_3$)$_3$), 1.6–2.4 (7H, m, 3×CH$_2$, 1×CH), 3.43 (2H, brs, CH$_2$N), 3.6 (1H, m, —CH—), 3.87 and 3.88 (total 3H, s×2, NCH$_3$, rotamers), 4.37 and 4.56 (total 1H, brs×2, —CHN, rotamers), 7.3–7.4 (3H, m, ArH), 7.80 and 7.83 (total 1H, s×2, H-2, rotamers), 8.23 (1H, d, J=7.5 Hz, H-4); m/z 408 (M+free base, 66%) 307 (30), 156 (100), 91 (60). Isomer B: m.p. 168°–169° C. Found: C, 67.63; H, 7.02; N, 13.61. C$_{23}$H$_{28}$N$_4$O$_3$ requires C, 67.63; H, 6.91; N, 13.72%; $\delta_H$ (360 MHz, CDCl$_3$) 1.19 and 1.33 (total 9H, s×2, C(CH$_3$)$_3$, rotamers), 1.85–2.45 (7H, m, 3×CH$_2$, 1×CH), 3.3–3.5 (2H, brm, CH$_2$N), 3.6–3.7 (1H, brm, —CH—), 3.86 (total 3H, s×2, NCH$_3$, rotamers), 4.32 and 4.45 (total 1H, brs×2, —CHN, rotamers), 7.25–7.38 (3H, m, ArH), 7.77 and 7.79 (total 1H, s×2, H-2, rotamers), 8.23 (1H, dd, J=7 Hz, H-4); m/z 408 (M+free base, 48%) 307 (35), 156 (100), 81 (55).

(c) (1R*,6R*)
6-[3-(1-Methylindol-3-yl)-1,2,4-oxadiazol-5-yl]-2-azabicyclo[2.2.2]octane hydrogen oxalate The above mentioned BOC-protected amine isomer A (0.19 g) was dissolved in anhydrous CH$_2$Cl$_2$ and trifluoroacetic acid (0.70 ml) added dropwise at 0° C. The mixture was allowed to warm up to room temperature with stirring for 3 hours, after which time the solvent was evaporated. The residue was dissolved in saturated K$_2$CO$_3$ solution (20 ml), extracted with CHCl$_3$ (7×15 ml), dried over (Na$_2$SO$_4$) and solvent evaporated to a glassy solid (0.15 g). This was further purified by treatment with a solution of oxalic acid in ether to give a precipitate of the title compound as a white crystalline solid, m.p. 218°–220° C. (dec). Found: C, 61.61; H, 6.03; N, 14.67; C$_{18}$H$_{20}$N$_4$O.¾ (COOH)$_2$.¼ H$_2$O requires C, 61.57; H, 5.83; N, 14.73%; $\delta_H$ (360 MHz, CF$_3$COOD) 1.6–2.3 (7H, m, 3×CH$_2$, CH), 3.34 (2H, brs, CH$_2$N), 3.56 (3H, s, NCH$_3$), 3.89 (1H, s, —CH—), 4.0 (1H, brt, CHN), 6.95–7.15 (3H, m, ArH), 7.54 (1H, s, H-2), 7.65 (1H, d, J=7.5 Hz, H-4); m/z 308 (M+free base, 5%) 156 (100), 82 (100).

(d) (1R*,6S*)
6-[3-(1-Methylindol-3-yl)-1,2,4-oxadiazol-5-yl]-2-azabicyclo[2.2.2]octane oxalate hemi hydrate The free base of the title compound was prepared as in Example 23C from the above mentioned BOC-protected amine isomer B (0.42 g) to yield a buff-coloured solid (0.33 g). The oxalate salt was prepared from 0.10 g as described in Example 23C above to give a white crystalline solid, m.p. 145°–146° C. (dec). Found: C, 59.09; H, 5.74; N, 13.47; C$_{18}$H$_{20}$N$_4$O.(COOH)$_2$.½H$_2$O requires C, 58.96; H, 5.69; N, 13.75%; $\delta_H$ (360 MHz, D$_2$O) 1.8–2.2 (6H, m, 3×CH$_2$), 2.4 (1H, brt, CH), 3.32 (2H, s, CH$_2$N), 3.6 (1H, m, —CH—), 3.86 (3H, s, NCH$_3$), 3.96 (1H, brs, CHN), 7.36 and 7.42 (2H, t×2, J=7.5, H-5, H-6), 7.58 (1H, d, J=8, H-7), 7.90 (1H, s, H-2), 8.00 (1H, d, J=8, H-4); m/z 308 (M+free base, 50%) 226 (25), 156 (100), 125 (20), 82 (55).

EXAMPLE 24

(1R*,6S*)
2-Methyl-6-[3-(1-methylindol-3-yl)-1,2,4-oxadiazol-5-yl]-2-azabicyclo[2.2.2]octane hydrogen oxalate (isomer A) and (1R*,6R*)
2-Methyl-6-[3-(1-methylindol-3-yl)-1,2,4-oxadiazol-5-yl]-2-azabicyclo[2.2.2]octane hydrogen oxalate (isomer B)

The isoquinuclidine free base (0.18 g) described in Example 23d was treated with formic acid (2.5 ml, 98% in H$_2$O) and formaldehyde (2.5 ml, 37% in H$_2$O) and heated at reflux for 1 hour; the solvents were removed at reduced pressure. The residual oil was washed with H$_2$O (10 ml) and saturated K$_2$CO$_3$ solution (10 ml), extracted with CH$_2$Cl$_2$ (6×15 ml), dried over anhydrous K$_2$CO$_3$ and evaporated to dryness. The 2 isomers were purified and separated by flash silica chromatography, eluting with CH$_2$Cl$_2$/MeOH (97:3) to afford isomer A (50 mg) and isomer B (50 mg) as waxy solids. Isomer A: $\delta_H$ (250 MHz, CDCl$_3$) 1.5–2.5 (8H, m, 3×CH$_2$ 2×CH), 2.26 (3H, s, NCH$_3$), 3.05–3.25 (3H, m, CH$_2$N, CH), 3.83 (3H, s, NCH$_3$), 7.23–7.38 (3H, m, ArH), 7.80 (1H, s, H-2), 8.23–8.27 (1H, m, H-4); m/z 322 (M+, 30%) 285 (40), 149 (90), 91 (100). Isomer B: $\delta_H$ (250 MHz, CDCl$_3$) 1.6–2.3 (7H, brm, 3×CH$_2$, CH), 2.50 (3H, s, NCH$_3$), 2.60 (1H, brd, CH), 2.95–3.03 (2H, m, CH$_2$N), 3.6–3.7 (1H, brm, CH), 3.87 (3H, s, NCH$_3$), 7.25–7.41 (3H, m, ArH), 7.82 (1H, s, H-2), 8.21–8.26 (1H, m, H-4); m/z 322 (M+. 60%) 156 (40), 94 (100). The oxalate salts were prepared as described in Example 23c. Isomer A: m.p. 169°–170° C. (dec). Isomer B: m.p. 65° C.

EXAMPLE 25

3[3-(1-Methylindol-3-yl)-1,2,4-oxadiazol-5-yl]-1-azabicyclo[2.2.1]heptane hydrogen oxalate hemihydrate (exo) and
3[3-(1-Methylindol-3-yl)-1,2,4-oxadiazol-5-yl]-1-azabicyclo[2.2.1]heptane hydrogen oxalate (endo)

This was prepared from [1-methylindol-3-yl]amide oxime (2.85 g) and 3-carbomethoxy-1-azabicyclo[2.2.1]heptane (1.6 g) using the method described in Example 3. The resulting oil was purified and the isomers separated by chromatography on Al$_2$O$_3$ (Merck, grade III) eluting with 2:1 CH$_2$Cl$_2$:EtOAc to afford the less polar exo isomer (1.20 g) and the more polar endo isomer (0.17 g) as yellow oils. The oxalate salts of both isomers were prepared as described in Example 23c. Exo isomer: m.p. 165°–166° C. (dec). Found: C, 57.85; H, 5.28; N, 14.06. C$_{17}$H$_{18}$N$_4$O.(COOH)$_2$.½H$_2$O requires C, 58.01; H, 5.37; N, 14.28%; $\delta_H$ (360 MHz, D$_2$O) 2.00–2.10 (1H, m, CHH), 2.25–2.35 (1H, m, CHH), 3.3–3.7 (6H, m, 2×CH$_2$N, 2×CH), 3.79 (3H, s, NCH$_3$), 3.80–3.90 (2H, m, CH$_2$N), 7.31 and 7.38 (2H, 2×dt, J=8, 1 Hz, H-5 and H-6), 7.50 (1H, d, J=8 Hz, H-7), 7.71 (1H, s, H-2), 7.88 (1H, dd, J=8, 1 Hz); m/z 294 (M+free base, 20%) 156 (100), 96 (65). Endo isomer: m.p. 152°–154° C. Found: C, 58.89; H, 5.28; N, 14.41; C$_{17}$H$_{18}$N$_4$O.(COOH)$_2$. (0.1) H$_2$O requires C, 59.09; H, 5.27; N, 14.51%; $\delta_H$ (250 MHz, D$_2$O) 1.6–1.7 (1H, m, CHH), 2.0–2.2 (1H, m, CHH), 3.3–3.6 (5H, brm, 2×CH$_2$N, CH), 3.7–3.8 (1H, m, CH), 3.79 (3H, s, NCH$_3$), 7.28–7.41 (2H, m, ArH), 7.50 (1H, d, J=8 Hz, H-7), 7.73 (1H, s, H-2), 7.89 (1H, d, J=8 Hz, H-4); m/z 294 (M+free base, 100%) 225 (60), 156 (60), 124 (50), 96 (45).

EXAMPLE 26

3[3-(1-Methylindol-3-yl)-1,2,4-thiadiazol-5-yl]-1-azabicyclo[2.2.2]octane hydrogen oxalate (a) Methyl (1-methylindol-3-yl)imidate hydrochloride Dry hydrogen chloride gas was bubbled through a solution of 1-methylindole-3-nitrile (17 g,) in dry methanol (100 ml). After standing at room temperature for 24 hr the solvent was evaporated at reduced pressure. The residue was triturated with cold ether/methanol to afford the title compound as white crystals (18 g, 88%), m.p. 156°–158° C. (dec); $\delta_H$ (360 MHz, DMSO-d$_6$) 3.4 (1H, s, NH), 3.9 (3H, s, NMe), 4.3 (3H, s, OMe), 7.3 (1H, dt, J=7.4, 1.2 Hz, CH), 7.4 (1H, dt, J=8.2, 1.6 Hz, CH), 7.7 (1H, d, J=7.8 Hz, CH), 7.9 (1H, dd, J=6.7, 1.1 Hz, CH), 9.0 (1H, s, CH); m/z 188 (M+).

(b) [1-Methylindol-3-yl]amidine hydrochloride

Dry ammonia gas was bubbled through a solution of the imidate (8.0 g) in dry methanol (120 ml) for 2 hours. After standing at room temperature for 24 hours the solvent was evaporated at reduced pressure to afford a buff coloured solid (7.5 g) contaminated with ~20% 1-methylindole-3-amide by ${}^1$H NMR. The title compound was used without further purification, m.p. 245°–250° C.; $\delta_H$ (250 MHz, DMSO-d$_6$) 3.91 (3H, s, NCH$_3$), 7.25–7.42 (2H, m, H-5, H-6), 7.61–7.67 (1H, dd, J=10, 2 Hz, H-7), 7.67–7.92 (1H, dd, J=2, 10 Hz, H-4), 8.40 (1H, s, H-2), 8.9–9.0 (3H, m, NH$_2$ and NH); m/z 173 (M+free base, 25%), 157 (100).

(c) 5-Chloro-3-(1-methylindol-3-yl)-1,2,4-thiadiazole

To an ice-cold, rapidly stirred two-phase mixture of the crude amidine (7.2 g) and perchloromethylmercaptan (5.1 g) in water (30 ml) and CH$_2$Cl$_2$ (40 ml) was added over 45 minutes a solution of NaOH (5.5 g) in water (30 ml). The mixture was allowed to warm to room temperature over 4 hours, the layers separated and the aqueous phase extracted with CH$_2$Cl$_2$ (3×30 ml). The combined organic portions were dried over Na$_2$SO$_4$, concentrated to dryness at reduced pressure and the resulting orange oil purified by flash silica chromatography, eluting with 1:1 hexane/CH$_2$Cl$_2$ to yield a yellow crystalline solid (4.2 g) m.p. 93°–94° C.; $\delta_H$ (250 MHz, CDCl$_3$) 3.67 (3H, s, NCH$_3$), 7.21–7.29 (3H, m, ArH), 7.74 (1H, s, H-2), 7.40–7.43 (1H, m, H-4); m/z 249 (M+, 100%), 188 (100), 156 (100).

(d) 3-[3-(1-Methylindol-3-yl)-1,2,4-thiadiazol-5-yl]-1-azabicyclo[2.2.2]octane hydrogen oxalate To a stirred solution of 3-carbomethoxyl-1-azabicyclo[2.2.2]octane (0.95 g) in anhydrous THF (60 ml) cooled to −78° C. was added LDA (5.0 ml of a 2.5M solution in cyclohexane) and kept at this temperature for 1 hour. The chlorothiadiazole (1.40 g) in THF (10 ml) was added and left to stir at −78° C. for 1½ hours before the mixture was allowed to warm to room temperature smoothly over 2 hours. Solvents were evaporated at reduced pressure to afford the crude ester as a viscous oil which was dissolved in MeOH (30 ml) and THF (20 ml) and treated with aqueous NaOH solution (30 ml, 2N) cooling in ice for 30 minutes. Volatile solvents were evaporated at reduced pressure and the aqueous solution extracted with EtOAc (3×30 ml). The aqueous layer was acidified to pH 2 with concentrated hydrochloric acid and stirred at room temperature for 2 hours, before basifying with saturated K$_2$CO$_3$ solution and extracting with CH$_2$Cl$_2$ (4×30 ml). The combined organic extracts were dried over Na$_2$SO$_4$ and solvent evaporated at reduced pressure to afford a brown oil which was purified by flash silica chromatography eluting with CH$_2$Cl$_2$/MeOH (92:8) to yield a glassy solid (0.11 g). Preparation of the oxalate salt as described above (Example 23C) gave the title compound as a white crystalline solid, $\delta_H$ (D$_2$O, 250 MHz) 1.7–1.9 and 2.1–2.2 (2×2H, 2×brs, 2×CH$_2$), 2.33 (1H, brs, CH), 3.3–3.5 (4H, brm, 2×CH$_2$N), 3.6–3.7 (3H, brs, CH$_2$N, —CH—), 3.76 (3H, s, NCH$_3$), 7.25–7.40 (2H, m, ArH), 7.45 (1H, d, J=11 Hz, H-7), 7.77 (1H, s, H-2), 8.14 (1H, d, J=11 Hz, H-4); m/z

EXAMPLE 27

3-[3-(1H-Indazol-3-yl)-1,2,4-oxadiazol-5-yl]-1-azabicyclo[2.2.2]octane hydrogen oxalate (a) [1H-Indazol-3-yl]amide oxime Hydroxylamine hydrochloride (1.5 g) and potassium carbonate (3.83 g) were stirred together in absolute ethanol (100 ml) for 15 minutes. Indazole-3-carbonitrile (2 g) was added and the solution heated at reflux for 4 hours, cooled to room temperature and diluted with methanol (5 ml). The solution was filtered and the solvent evaporated. The residue was extracted with anhydrous ether, the extracts were dried over MgSO$_4$, filtered and the solvent removed to afford a white solid, which was recrystallised from acetone/dichloromethane to afford the title compound (900 mg), m.p. 155°–158° C. $\delta_H$ (360 MHz, CDCl$_3$) 6.46 (1H, brm, N-OH), 7.17 (1H, t, J=1 Hz, H-6), 7.41 (1H, t, J=2 Hz, H-5), 7.55 (1H, d, J=2 Hz, H-4), 8.03 (1H, t, J=2 Hz, H-7); m/z (M+, 100%), 176 (100), 144 (80), 119 (25), 92 (15).

(b) 3-[3-(1H-Indazol-3-yl)-1,2,4-oxadiazol-5-yl]-1-azabicyclo[2.2.2]octane hydrogen oxalate

[1H-Indazol-3-yl]amide oxime (190 mg) was dissolved in anhydrous tetrahydrofuran (50 ml) to which was added 4A molecular sieves. After stirring for 15 minutes sodium hydride (100 mg of 55% dispersion in oil) was added and the mixture stirred for a further 15 minutes before the addition of 3-carbomethoxy-1-azabicyclo[2.2.2]octane (400 mg). The resulting mixture was then heated at reflux for six hours, then cooled to room temperature. Methanol (10 ml) was added, the solution filtered and the solvent evaporated. The residue was purified by chromatography on silica using CH$_2$Cl$_2$/CH$_3$OH/NH$_4$OH 90/10/1 as eluant to afford a colourless oil (300 mg). This was further purified by treatment with a solution of oxalic acid in acetone to afford the title compound, m.p. 215° C. (dec). Found: C, 58.22; H, 5.44; N, 19.41. C$_{18}$H$_{17}$N$_5$O$_6$ requires C, 57.92; H, 5.13; N, 19.30%; $\delta_H$ (360 MHz, D$_2$O) 1.98 (2H, m, CH$_2$CH$_2$—N), 2.26 (2H, m, CH$_2$CH$_2$—N), 2.75 (1H, m, CH—CH$_2$CH$_2$—N), 3.51 (3H, m, CH$_2$CH$_2$N), 3.97 (3H, m, CH$_2$CH$_2$N), 7.35 (1H, t, J=4 Hz, H-6), 7.54 (1H, t, J=4.9 Hz, H-5), 7.68 (1H, d, J=4 Hz, H-7), 8.03 (1H, d, J=4 Hz, H-4); m/z (M+, free base 95%) 295 (95), 238 (15), 212 (100), 159 (40), 143 (35), 96 (70), 83 (60).

EXAMPLE 28

3-[3-(1H-indol-3-yl)-1,2,4-oxadiazol-5-yl]-1-azabicyclo[2.2.2]octane hydrochloride

(a) [1H-indol-3-yl]amide oxime 0.25 hydrate 1H-indole-3-nitrile (25.45 g,) and potassium carbonate (49.77 g,) were added to a solution of hydroxylamine hydrochloride (18.77 g,) in ethanol (600 ml) under nitrogen. After heating under reflux for 6 hours the mixture was filtered while hot and the precipitates washed with ethanol. The filtrate and washings were combined and evaporated to dryness. The residue was purified by flash chromatography eluting with acetone/dichloromethane mixtures. Recrystallisation from acetone/dichloromethane gave the title compound m.p. 154°-156° C. Found: C, 60.36; H, 5.15; N, 23.42; $C_9H_9N_3O.0.25H_2O$ requires C, 60.16; H, 5.33; N, 23.38% $\delta_H$ (360 MHz, DMSO-$d_6$) 5.56 (2H, s, $NH_2$), 7.00 (1H, dt, J=8.0 and 1.0, CH), 7.10 (1H, dt, J=8.2 and 1.2, CH), 7.36 (1H, d, J=8.0, CH), 7.75 (1H, d, J=2.1, CH), 8.05 (1H, d, J=7.8, CH), 9.18 (1H, s,) and 11.20 (1H, s, exchangeable protons); m/z 175 ($M^+$).

(b) 3-[3-(1H-indol-3-yl)-1,2,4-oxadiazol-5-yl]-1-azabicyclo[2.2.2]octane hydrochloride A mixture of 1-azabicyclo[2.2.2]octane-3-carboxylic acid hydrochloride (0.89 g,) and molecular sieves (2.0 g) was stirred in dry dimethylformamide (50 ml) for 30 minutes. Triethylamine (1.4 ml,) was added and, after chilling, ethyl chloroformate (0.5 ml,) followed by a solution of [1H-indol-3-yl]amide oxime (0.85 g, 4.9 mmol) in dimethylformamide (10 ml). After stirring at room temperature for two hours and heating to 120° C. for 2 hours the mixture was cooled, filtered through hyflo and evaporated to dryness. The residue was taken up in 2N hydrochloric acid and washed with dichloromethane. After basification with 8% ammonia solution, the aqueous phase was extracted with dichloromethane. The extracts were dried ($MgSO_4$) and solvents evaporated. Addition of methanol and methanolic hydrogen chloride gave the title compound; m.p. 226°-228° C. $\delta_H$ (360 MHz, $D_2O$) 1.88-2.04 (2H, m, $CH_2$), 2.14-2.28 (2H, m, $CH_2$), 2.68-2.74 (1H, m, CH), 3.36-3.54 (4H, m, 2×$CH_2$), 3.78-3.96 (3H, m, $CH_2$+CH), 7.34-7.42 (2H, m, 2×CH), 7.65 (1H, d, J=7.2, CH), 8.07 (1H, d, J=5.9, CH) and 8.08 (1H, s, CH); m/z 294 ($M^+$).

EXAMPLE 29

3-[3-(1,7-Dimethylindol-3-yl)-1,2,4-oxadiazol-5-yl]-1-azabicyclo[2.2.2]octane hydrogen oxalate

(a) 1,7-Dimethylindole-3-carboxylic acid

Methyl iodide (30 g) was added to a stirred mixture of 7-methylindole-3-carboxylic acid (4.3 g) and powdered potassium hydroxide (20 g) in anhydrous acetone at 0° C. The resulting suspension was then stirred at room temperature overnight, then poured into water (500 ml), washed with dichloromethane (3×100 ml) and the aqueous phase acidified to pH 2 with hydrochloric acid. The product was isolated by filtration and dried under vacuum to afford white crystals (4.5 g); m.p. 243° C.; $\delta_H$ (360 MHz, DMSO-$d_6$) 2.72 (3H, s, $CH_3$), 4.09 (3H, s, $NCH_3$), 6.92 (1H, d, J=6 Hz, H-6), 7.02 (1H, t, J=6 Hz, H-5), 7.87 (1H, d, J=6, H-4), 7.92 (1H, s, H-2); m/z 189 ($M^+$, 100%), 172 (40), 144 (30), 91 (55).

(b) 1,7-Dimethyindole-3-carboxamide

Oxalyl chloride (6.0 g) was added dropwise to a stirred solution of 1,7-dimethylindole-3-carboxylic acid (4.5 g) in tetrahydrofuran (50 ml) at 0° C. After the addition the solution was stirred for 12 hrs at room temperature. The solvent was then evaporated at reduced pressure and the residue dissolved in dichloroethane (100 ml) and ammonia bubbled through the solution for five hours. The solvent was then removed at reduced pressure and the residue triturated with water (20 ml) and ether (2×50 ml) to yield a white solid (4.4 g); m.p. 197° C.; $\delta_H$ (360 MHz, DMSO-$d_6$) 2.72 (3H, s, $CH_3$), 4.03 (3H, s, $NCH_3$), 6.67 (1H, d, J=6 Hz, H-6), 6.96 (1H, t, J=6 Hz, H-5), 7.86 (1H, s, H-2), 8.00 (1H, d, J=6 Hz, H-4); m/z 188 ($M^+$, 55%), 172 (100), 88 (40).

(c) 1,7-Dimethylindole-3-nitrile

Trifluoroacetic anhydride (20 g) was added dropwise to a stirred solution of the amide (4.4 g) in dioxane (200 ml) and triethylamine (19 g) at 0° C. The resulting mixture was then stirred at room temperature for 12 hr. The resulting solution was diluted with dichloromethane (500 ml) and washed with water (3×200 ml), the organic phase was then dried ($MgSO_4$) and the solvent evaporated. The residue was purified by chromatography on silica, eluting with dichloromethane affords a white solid (3 g); m.p. 116° C.; $\delta_H$ (360 MHz, $CDCl_3$) 2.75 (3H, s, $CH_3$), 4.08 (3H, s, $NCH_3$), 7.02 (1H, d, J=6 Hz, H-6), 7.14 (1H, t, J=6 Hz, H-5), 7.43 (1H, s, H-2), 7.56 (1H, d, J=6 Hz, H-4); m/z 170.0840 ($M^+$, $C_{11}H_{10}N_2$ requires 170.0844, 100%).

(d) [1,7-Dimethylindol-3-yl]amide oxime

Potassium carbonate (6 g) was added to a stirred solution of the nitrile (2.7 g) and hydroxylamine hydrochloride (2 g) in dry methanol (100 ml). The solution was heated at reflux for 12 hr, then cooled to 0° C. and filtered. The solvent was then evaporated at reduced pressure and the residue purified by chromatography on silica eluting with dichloromethane/acetone (1:1) to afford a white solid (0.5 g); m.p. 177°-180° C.; $\delta_H$ (360 MHz, DMSO-$d_6$) 2.74 (3H, s, $CH_3$), 4.02 (3H, s, $NCH_3$), 6.13-6.90 (2H, m, H-5, H-6), 7.58 (1H, s, H-2), 7.91 (1H, d, J=6 Hz, H-4); m/z 203.1070 ($M^+$, $C_{11}H_{13}N_3O$ requires 203.1059, 80%), 170(100).

(e) 3-[3-(1,7-Dimethylindol-3-yl)-1,2,4-oxadiazol-5-yl]-1-azabicyclo[2.2.2]octane hydrogen oxalate This was prepared from [1,7-dimethylindol-3-yl]amide oxime (0.4 g) and 3-carbomethoxy-1-azabicyclo[2.2.2]octane (0.5 g) using the procedure described in Example 3. This was purified by chromatography on alumina eluting with dichloromethane/methanol (98:2). Formation of the oxalate salt as described previously gave the title compound as white crystals (0.4 g); m.p. 146° C.; $\delta_H$ (360 MHz, DMSO-$d_6$) 1.75-2.2 (4H, m, 2×$CH_2$), 2.54 (1H, brs, CH), 2.77 (3H, s, $CH_3$), 3.2-3.3 (4H, m, 2×$CH_2$), 3.65-3.85 (3H, m, $CH_1CH_2$), 4.15 (3H, s, $NCH_3$), 6.98 (1H, d, J=6 Hz, H-6), 7.08 (1H, t, J=6 Hz, H-5), 7.88 (1H, d, J=6 Hz, H-4), 8.06 (1H, s, H-2); m/z 322 ($M^+$ free base, 30%), 239 (35), 170 (100), 169 (55).

EXAMPLE 30

4-[2-(1-Methylindol-3-yl)-1,3,4-oxadiazol-5-yl]-1-methyl-1,2,5,6-tetrahydropyridine hydrochloride

(a) 4-[2-(1-Methylindol-3-yl)-1,3,4-oxadiazol-5-yl]pyridine

Methyl [1-methylindol-3-yl]imidate hydrochloride (example 26A) (3.0 g) and isonicotinic acid hydrazide (1.84 g) were dissolved in absolute ethanol (100 ml), heated at reflux for 60 hours, cooled to room temperature and evaporated to dryness. The residue was taken up in water (200 ml), extracted with dichloromethane (4×100 ml), dried over MgSO$_4$, and the solvent removed to give a yellow solid. Recrystallisation from ethanol gave the title compound as white needles (1.7 g) m.p. 212°–214° C.; Found: C, 69.39; H, 4.38; N, 20.16; C$_{16}$H$_{12}$N$_4$O requires C, 69.39; H, 4.38; N, 20.16%; $\delta_H$ (CDCl$_3$) 3.02 (3H, s, N-CH$_3$), 7.3–7.45 (3H, brm, H-4,5,6), 7.89 (1H, s, H-2), 7.99 (2H, dd, J=5.1 Hz, CH=CH—N), 8.27–8.34 (1H, brm, H-7), 8.83 (2H, dd, J=5, 1 Hz, CH=CH—N); m/z (M+, 30%) 276 (30), 158 (100), 130 (15), 91 (20), 77 (30).

(c) 4-[2-(1-Methylindol-3-yl)-1,3,4-oxadiazol-5-yl]-1-methylpyridinium iodide 4-[2-(1-methylindol-3-yl)-1,3,4-oxadiazol-3-yl]pyridine (50 mg) was dissolved in dry acetone (10 ml), methyl iodide (127 mg) was then added, and the resulting solution heated at reflux for twenty four hours under a dry nitrogen atmosphere. The solution was allowed to cool to room temperature and the yellow solid isolated by filtration. Recrystallisation from acetone afforded the title compound (70 mg); m.p. 290° C. (dec); Found: C, 47.85; H, 3.56; N, 13.12; C$_{17}$N$_{16}$N$_4$O$_{15}$I requires C, 47.79; H, 3.77; N, 13.11%; $\delta_H$ (360 MHz, DMSO-d$_6$) 3.98 (3H, s, N—CH$_3$), 4.43 (3H, s, $^+$N—CH$_3$), 7.38 (2H, brm, H-5,6), 7.68 (1H, brm, H-4), 8.24 (1H, brm, H-7), 8.49 (1H, s, H-2), 8.70 (2H, d, J=8.4 Hz, CH=CH—N), 9.18 (2H, d, J=8.4 Hz, CH=CH—N); m/z (M+ free base 60%,) 276 (60), 158 (100), 127 (20), 103 (10), 77 (10).

(d) 4-[2-(1-Methylindol-3-yl)-1,3,4-oxadiazol-5-yl]-1-Methyl-1,2,5,6-tetrahydropyridine hydrogen chloride 4-[2-(1-methylindol-3-yl)-1,3,4-oxadiazol-5-yl]-1-methylpyridinium iodide (1.0 g) was suspended in a mixture of ethanol (50 ml) and water (5 ml) with vigorous stirring. NaBH$_4$ (200 mg) was added portionwise until the solution was clear and colourless. The solution was stirred for one hour at room temperature. 2N Hydrochloric acid (10 ml) was added to quench the excess NH$_4$OH, followed by 0.88 NH$_3$ to pH 12, the solution was then extracted with dichloromethane (4×100 ml), dried over MgSO$_4$ and evaporated to dryness. The residue was purified by chromatography on silica eluting with methanol/dichloromethane (2:98). The isolated product was treated with an excess of ethereal HCl, recrystallisation from absolute methanol afforded the title compound as a white solid m.p. 245°–250° C. Found: C, 61.35; H, 5.85; N, 16.74; C$_{17}$H$_{18}$N$_4$OCl requires C 61.72; H, 5.78; N, 16.93%; $\delta_H$ (360 MHz, D$_2$O 2.67 (2H, bm, CH$_2$—N—CH$_3$), 3.07 (3H, s, N—CH$_3$), 3.4 (2H, brm, CH$_2$N—CH$_3$), 3.55 (3H, s, N—CH$_3$), 3.48 (2H, brm, CH$_2$CH$_2$N), 6.27 (1H, brm, C=CH—CH$_2$), 7.09 (2H, brm, H-5,6), 7.11 (1H, d, J=5 Hz, H-4), 7.22 (1H, s, H-2), 7.35 (1H, d, J=5 Hz, H-7); m/z 294 (M+ free base, 100%), 158 (40), 110 (30), 94 (30), 77 (10).

EXAMPLE 31

3-[2-(1-Methylindol-3-yl)-1,3-thiazol-4-yl]-1-methyl-1,2,5,6-tetrahydropyridinium hydrochloride

(a) 1-Methylindole-3-thiocarboxamide

1-Methylindole-3-carboxamide (0.6 g) was suspended in toluene (20 ml); Lawesson's Reagent (0.7 g) was added and the mixture was heated at reflux under nitrogen for 30 min until dissolution occurred. The solution was cooled and toluene was removed under reduced pressure. The orange residue was purified by column chromatography on alumina using CH$_2$Cl$_2$ as eluant. This afforded an orange crystalline material, (0.5 g). $\delta_H$ (360 MHz, DMSO-d$_6$) 3.82 (3H, s, NCH$_3$), 7.18 and 7.23 (2H, 2×dt, J=7.1, 1.1 Hz, H-5 and H-6), 7.49 (1H, d, J=7.5 Hz, H-7), 8.08 (1H, s, H-2), 8.59 (1H, d, J=7.5 Hz, H-4), 8.76 (2H, brs, NH$_2$); m/z 190 (M+, 100%), 174 (20), 157 (80).

(b) 3-[2-(1-Methylindol-3-yl)-1,3-thiazol-4-yl]pyridinium hydrobromide

1-Methylindole-3-thiocarboxamide (0.5 g) was dissolved in anhydrous DMF (5 ml). This solution was added to a stirred suspension of 3-bromoacetylpyridinium hydrobromide (1.1 g) in anhydrous DMF (2 ml). This was stirred for 10 minutes at room temperature. The title compound was isolated by filtration and was washed thoroughly with ether, 0.5 g. $\delta_H$ (360 MHz, DMSO-d$_6$) 3.91 (3H, s, NCH$_3$), 7.2–7.4 (2H, m, H-5 and H-6), 7.58 (1H, d, J=7.4 Hz, H-7), 8.03 (1H, dd, J=5.5, 8.1 Hz, H-5" β-pyr), 8.26 (1H, s, H-5' thiazole), 8.36 (1H, d, partially buried, H-4), 8.38 (1H, s, H-2), 8.83 (1H, mc, H-4" γ-pyr), 8.99 (1H, d, J=8.2 Hz, H-6" α-pyr), 9.47 (1H, mc, H-2" α-pyr); m/z 291 (M+, 100%), 135 (30).

(c) 3-[2-(1-Methylindol-3-yl)-1,3-thiazol-4-yl]-1-methylpyridinium iodide

The hydrobromide above was liberated as the free base by treatment with methanolic K$_2$CO$_3$. The residue was suspended in water and extracted with dichloromethane. The organic phase was dried (MgSO$_4$) and evaporated under reduced pressure; the resulting solid was purified by flash chromatography on silica using 10% ethyl acetate in dichloromethane affording a pale yellow solid (0.6 g). This was dissolved in acetone (25 ml) and methyl iodide (1 ml) was added to the stirred solution. After 5 min a crystalline precipitate was observed. This was isolated by filtration and was washed with ether and dried, yielding 0.85 g of a bright yellow crystalline material, m.p. 250° C. (dec). Found: C, 49.90; H, 3.71; N, 9.65. C$_{18}$H$_{16}$N$_3$SI requires C, 49.89; H, 3.72; N, 9.70%. $\delta_H$ (360 MHz, DMSO-d$_6$) 3.91 (3H, s, NCH$_3$), 4.48 (3H, s, NCH$_3$ pyr), 7.29–7.36 (2H, m, H-5 and H-6), 7.59 (1H, dd, J=6.4, 1.5 Hz, H-7), 8.22 (1H, dd, J=6.1, 6.0 Hz, H-5" β-pyr), 8.27 (1H, s, H-5' thiazole), 8.40 (1H, dd, H-4 partially hidden), 8.41 (1H, s, H-2), 8.94 (1H, d, J=6.0 Hz, H-4" β-pyr), 9.13 (1H, d, J=8.1 Hz, H-6" α-pyr), 9.59 (1H, s, H-2" α-pyr); m/z 291 (M+, 40%), 220 (80), 169 (100).

(d)

3-[2-(1-Methylindol-3-yl)-1,3-thiazol-4-yl]-1-methyl-1,2,5,6-tetrahydropyridinium hydrochloride 3-[2-(1-Methylindol-3-yl)-1,3-thiazol-4-yl]-1-methylpyridinium iodide (0.8 g) was suspended in ethanol (20 ml) and water (1 ml). Sodium borohydride (0.1 g) was added in portions with much evolution of hydrogen. After 30 minutes the intense yellow coloration was replaced by a light brown hue. 5M Hydrochloric acid was added dropwise to quench excess sodium borohydride. The contents of the flask were poured onto a saturated solution of sodium bicarbonate which was extracted with dichloromethane (4×150 ml). This was washed with brine, dried (MgSO$_4$) and evaporated under reduced pressure. The residue was purified by column chromatography on silica using 10% methanol in dichloromethane as eluant yielding 0.4 g. This was further purified by dissolving in methanol; addition of methanolic HCl (20 ml) precipitated the hydrochloride as a yellow powder. This was recrystallised from aqueous ethanol, m.p. 235° C. (dec). $\delta_H$ 2.6–2.8 (2H, m, β-pyr), 3.08 (3H, s, NMe pyr), 3.16–3.28 (1H, m, α-pyr), 3.65 (1H, mc, α-pyr), 3.74 (1H, d, J=15.6 Hz, H-1 α-pyr), 4.14 (1H, d, J=15.6 Hz, H-1 α-pyr), 6.53 (1H, mc, H-4 γ-pyr), 7.09 (1H, s, SCH), 7.23 and 7.30 (2H, 2×t, J=7.9 Hz, H-5 and H-6), 7.37 (1H, d, J=7.9 Hz), 7.53 (1H, d, J=7.8 Hz), 7.75 (1H, s, H-2); m/z 309 (M+ free base, 100%), 265 (40), 168 (40), 96 (35).

EXAMPLE 32

3[3-(1-Methylindol-3-yl)-1,2,4-thiadiazol-5-yl]-1-azabicyclo[2.2.1]heptane hydrogen oxalate (exo) and 3[3-(1-Methylindol-3-yl)-1,2,4-thiadiazol-5-yl]-1-azabicyclo[2.2.1]heptane hydrogen oxalate (endo)

These were prepared from 5-chloro-3-(1-methylindol-3-yl)-1,2,4-thiadiazole (2.6 g) and 3-carbomethoxy-1-azabicyclo[2.2.1]heptane (1.8 g) using the method described in Example 26 d. The resulting oil was purified and the isomers separated by flash silica gel chromatography eluting with 95:5 CH$_2$Cl$_2$:MeOH to afford the less polar exo isomer (0.18 g) and the more polar endo isomer (0.49 g) as crystalline solids. The oxalate salts were prepared by addition of an ethereal solution of oxalic acid to the free bases dissolved in CH$_2$Cl$_2$ to give both isomers as white crystalline solids. Exo isomer: m.p. 171°–172° C. (dec); $\delta_H$ (250 MHz, D$_2$O) 1.9–2.0 and 2.2–2.3 (2H, brm, CH$_2$), 3.1–3.8 (8H, brm, 3×CH$_2$N, 2×CH), 3.81 (3H, s, NCH$_3$), 7.26–7.40 (2H, m, ArH), 7.49 (1H, d, J=8 Hz, H-7), 7.81 (1H, s, H-2), 8.15 (1H, d, J=7 Hz, H-4); m/z 310 (M+ free base 100%) 188 (30), 156 (95). Endo isomer: m.p. 195°–196° C. (dec). Found: C, 56.30; H, 5.06; N, 13.75; C$_{17}$H$_{18}$N$_4$S. (COOH)$_2$. ¼H$_2$O requires C, 56.35; H, 5.10; N, 13.84%; $\delta_H$(250 MHz, D$_2$O) 1.7–1.8 and 2.0–2.1 (2H, brm, CH$_2$), 3.4–3.6 (5H, m, 2×CH$_2$N, CH), 3.7–3.8 (1H, m, CHHN), 3.85 (3H, s, NCH$_3$), 3.8–4.0 (1H, m, CHHN), 4.25–4.35 (1H, brm, CH), 7.3–7.4 (2H, m, ArH), 7.54 (1H, d, J=8 Hz, H-7), 7.94 (1H, s, H-2), 8.24 (1H, d, J=7 Hz, H-4); m/z 310 (M+ free base 100%) 188 (30), 156 (90).

EXAMPLE 33

3[3-(1H-Indol-2-yl)-1,2,4-oxadiazol-5-yl]-1-azabicyclo[2.2.2]octane hydrogen oxalate (a) [1H-Indol-2-yl]amide oxime 1H-Indol-2-nitrile (0.39 g) was heated at reflux in ethanol (25 ml) with hydroxylamine hydrochloride (0.29 g) and potassium carbonate (0.76 g) for 3 hours. The solvent was evaporated at reduced pressure to yield the crude product as a buff coloured solid (0.44 g) which was used without further purification. $\delta_H$ (250 MHz, DMSO-d$_6$) 3.32 (3H, s, NCH$_3$), 5.83 (2H, br s, NH$_2$), 6.84 (1H, m, H-3), 6.9–7.5 (4H, m, ArH); m/z 175 (M+, 60%) 142 (100).

(b)

3-[3-(1H-Indol-2-yl)-1,2,4-oxadiazol-5-yl]-1-azabicyclo[2.2.2]octane hydrogen oxalate This was prepared from [1H-Indol-2-yl]amide oxime (0.43 g) and 3-carbomethoxy-1-azabicyclo[2.2.2]octane (0.83 g) using the method described in Example 3. The resulting solid was purified by silica gel chromatography eluting with 97:3 CH$_2$Cl$_2$/MeOH. This was further purified by formation of the oxalate salt to afford the title compound (0.30 g), m.p. 180°–182° C. (dec); Found: C, 56.02; H, 5.21; N, 13.14; requires C, 55.94; H, 4.92; N, 13.05%. $\delta_H$ (360 MHz, CF$_3$COOD).

EXAMPLE 34

Tablet Preparation

Tblets containing 1.0, 2.0, 25.0, 26.0, 50.0 and 100.0 mg, respectively, of the following compounds are prepared as illustrated below:

3-[3-1-(Methylindol-3-yl)-1,2,4-oxadiazol-5-yl]-1-azabicyclo[2.2.2]octane.

1-Methyl-4-[3-(1-methylindol-3-yl)-1,2,4-oxadiazol-5-yl]piperidine.

3-[3-(-1Methylindol-3-yl)-1,2,4-oxadiazol-5-yl]-8-methyl-8-azabicyclo[3.2.1]octane.

1-Methyl-3-[5-dimethylaminoethyl-1,2,4-oxadiazol-3-yl]indole.

3-[3-(1-Methylindol-3-yl]-1,2,4-oxadiazol-5-yl]-2-azabicyclo[2.2.2]octane.

3-[3-(1-Methylindol-3-yl)-1,2,4-thiadiazol-5-yl]-1-azabicyclo[2.2.2]octane.

3-[3-(1-Methylindol-3-yl)-1,2,4-oxadiazol-5-yl]-8-methyl-8-azabicyclo[3.2.1]octane

TABLE

| | Amount-mg | | |
|---|---|---|---|
| TABLE FOR DOSES CONTAINING FROM 1–25 MG OF THE ACTIVE COMPOUND | | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| TABLE FOR DOSES CONTAINING FROM 26–100 MG OF THE ACTIVE COMPOUND | | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0

What is claimed is:

1. A compound represented by the formula IV or a salt thereof:

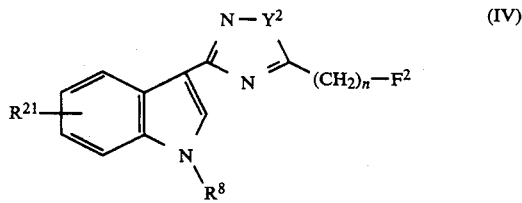

wherein $R^8$ is selected from the group consisting of hydrogen, $C_{1-6}$ alkyl, $C_{2-6}$ alkenyl and $C_{2-6}$ alkynyl; $Y^2$ represents oxygen or sulphur; n is zero, 1 or 2; $R^{21}$ is selected from the group consisting of hydrogen, halogen, cyano and $C_{1-6}$ alkyl; and $F^2$ represents a non-aromatic azamonocyclic or azabicyclic ring system containing from 4 to 10 atoms, with one nitrogen atom as the sole heteroatom.

2. A compound according to claim 1 wherein $F^2$ is selected from the group consisting of pyrrolidine, piperidine, tetrahydropyridine, azanorbornane, quinuclidine, isoquinuclidine, azabicyclo[3.2.1]octane and azabicyclo[3.3.1]nonane, any of which may be optionally substituted with methoxy, methyl or hydroxy.

3. A compound according to claim 2 selected from the group consisting of
3-[3-(1-methylindol-3-yl)-1,2,4-oxadiazol-5-yl]-1-azabicyclo[2.2.2]octane;
2-[3-(1-methylindol-3-yl)-1,2,4-oxadiazol-5-yl]-1-azabicyclo[2.2.2]octane;
1-methyl-4-[3-(1-methylindol-3-yl)-1,2,4-oxadiazol-5-yl]piperidine;
1,1-dimethyl-4-[3-(1-methylindol-3-yl)-1,2,4-oxadiazol-5-yl]piperidinium iodide;
1-methyl-3-[3-(1-methylindol-3-yl)-1,2,4-oxadiazol-5-yl]piperidine;
1,1-dimethyl-3-[3-(1-methylindol-3-yl)-1,2,4-oxadiazol-5-yl]piperidinium iodide;
3-[3-(5-fluoro-1-methylindol-3-yl)-1,2,4-oxidazol-5-yl]-1-azabicyclo[2.2.2]octane;
3-[3-(1-methylindol-3-yl)-1,2,4-oxadiazole-5-yl]-8-methyl-8-azabicyclo[3.2.1]octane;
3-[3-(1-methylindol-3-yl)-1,2,4-oxadiazol-5-yl]-1,2,5,6-tetrahydropyridine;
3-[3-(methylindol-3-yl)-1,2,4-oxadiazol-5-yl]-1-methyl-1,2,5,6-tetrahydropyridine;
3-[3-(1-methylindol-3-yl)-1,2,4-oxadiazol-5-yl]-1-aza-2-methoxybicyclo[2.2.2]octane;
1-methyl-3-[5-(2-(1-piperidyl)ethyl)-1,2,4-oxadiazol-3-yl]indole;
6-[3-(1-methylindol-3-yl)-1,2,4-oxadiazol-5-yl]-2-azabicyclo[2.2.2]octane;
2-methyl-6-[3-(1-methylindol-3-yl)-1,2,4-oxadiazol-5-yl]-2-azabicyclo[2.2.2]octane;
3-[3-(1-methylindol-3-yl)-1,2,4-oxadiazol-5-yl]-1-azabicyclo[2.2.1]heptane;
3-[3-(1-methylindol-3-yl)-1,2,4-thiadiazol-5-yl]-1-azabicyclo[2.2.2]octane;
3-[3-(1H-indol-3-yl)-1,2,4-oxadiazol-5-yl]-1-azabicyclo[2.2.2]octane;
3-[3-(1,7-dimethylindol-3-yl)-1,2,4-oxadiazol-5-yl]-1-azabicyclo[2.2.2]octane;
3-[3-(1-methylindol-3-yl)-1,2,4-thiadiazol-5-yl]-1-azabicyclo[2.2.1]heptane;
or a salt thereof.

4. A pharmaceutical composition for the treatment of psychotic disorders; anxiety; alcohol or drug withdrawal; pain; gastric stasis; gastric dysfunction; migraine, nausea and vomiting; and presenile and senile dementia; comprising an effective amount of a compound according to claim 1 in association with a pharmaceutically acceptable carrier or excipient.

5. A method for the treatment of psychotic disorders; anxiety; alcohol or drug withdrawal; pain; gastric dysfunction; migraine, nausea and vomiting; and presenile and senile dementia; which method comprises administering to a patient in need of such treatment an effective amount of a compound according to claim 1.

* * * * *